(12) United States Patent
Kyle et al.

(10) Patent No.: US 8,609,945 B1
(45) Date of Patent: Dec. 17, 2013

(54) SOYBEAN VARIETY XB33H12

(75) Inventors: Donald Kyle, Princeton, IL (US); Thomas C. Corbin, Monticello, IL (US)

(73) Assignee: Pioneer Hi Bred International Inc, Johnston, IA (US)

( * ) Notice: Subject to any disclaimer, the term of this patent is extended or adjusted under 35 U.S.C. 154(b) by 0 days.

(21) Appl. No.: 13/409,227

(22) Filed: Mar. 1, 2012

(51) Int. Cl.
*A01H 5/00* (2006.01)
*C12N 15/82* (2006.01)

(52) U.S. Cl.
USPC .......................... 800/312; 435/415; 435/468

(58) Field of Classification Search
None
See application file for complete search history.

(56) References Cited

U.S. PATENT DOCUMENTS

| | | | | |
|---|---|---|---|---|
| 7,081,569 | B2 * | 7/2006 | Ivers | 800/312 |
| 7,169,979 | B2 | 1/2007 | Steiger et al. | |
| 2012/0240265 | A1 * | 9/2012 | Steiger et al. | 800/260 |

OTHER PUBLICATIONS

Plant Variety Protection certificate No. 200700110 for Soybean Variety 93M61, issued Aug. 3, 2007.
Plant Variety Protection certificate No. 200800153 for Soybean Variety RJS34001, issued Jan. 22, 2009.
Plant Variety Protection certificate No. 201100176 for Soybean Variety 93Y84, filed Jan. 27, 2011.
Plant Variety Protection certificate No. 201100239 for Soybean Variety RJS37007, filed Jan. 27, 2011.
Plant Variety Protection certificate No. 201200223 for Soybean Variety XB33H12, filed Mar. 16, 2012.
Plant Variety Protection certificate No. 201200227 for Soybean Variety XB37K12, filed Mar. 16, 2012.
Plant Variety Protection certificate No. 201200228 for Soybean Variety XB37U12, filed Mar. 16, 2012.
Plant Variety Protection certificate No. 201200273 for Soybean Variety RJS37008, filed Mar. 16, 2012.
U.S. Appl. No. 13/047,935, filed Mar. 15, 2011, Kyle, Donald, et al.
U.S. Appl. No. 13/047,872, filed Mar. 15, 2011, Streit, Leon G, et al.
U.S. Appl. No. 13/409,215, filed Mar. 1, 2012, Corbin, Thomas C, et al.
U.S. Appl. No. 13/409,208, filed Mar. 1, 2012, Corbin, Thomas C, et al.
U.S. Appl. No. 13/409,262, filed Mar. 1, 2012, Kallem, Randy L, et al.

* cited by examiner

*Primary Examiner* — Vinod Kumar

(57) ABSTRACT

A novel soybean variety, designated XB33H12 is provided. Also provided are the seeds of soybean variety XB33H12, cells from soybean variety XB33H12, plants of soybean XB33H12, and plant parts of soybean variety XB33H12. Methods provided include producing a soybean plant by crossing soybean variety XB33H12 with another soybean plant, methods for introgressing a transgenic trait, a mutant trait, and/or a native trait into soybean variety XB33H12, methods for producing other soybean varieties or plant parts derived from soybean variety XB33H12, and methods of characterizing soybean variety XB33H12. Soybean seed, cells, plants, germplasm, breeding lines, varieties, and plant parts produced by these methods and/or derived from soybean variety XB33H12 are further provided.

19 Claims, No Drawings

SOYBEAN VARIETY XB33H12

FIELD OF INVENTION

This invention relates generally to the field of soybean breeding, specifically relating to a soybean variety designated XB33H12.

BACKGROUND

The present invention relates to a new and distinctive soybean variety designated XB33H12, which has been the result of years of careful breeding and selection in a comprehensive soybean breeding program. There are numerous steps in the development of any novel, desirable soybean variety. Plant breeding begins with the analysis and definition of problems and weaknesses of the current germplasm, the establishment of program goals, and the definition of specific breeding objectives. The next step is selection of germplasm that possess the traits to meet the program goals. The breeder's goal is to combine in a single variety an improved combination of desirable traits from the parental germplasm. These important traits may include, but are not limited to: higher seed yield, resistance to diseases and/or insects, tolerance to drought and/or heat, altered fatty acid profile(s), abiotic stress tolerance, improvements in compositional traits, and better agronomic characteristics.

These product development processes, which lead to the final step of marketing and distribution, can take from six to twelve years from the time the first cross is made until the finished seed is delivered to the farmer for planting. Therefore, development of new varieties is a time-consuming process that requires precise planning, efficient use of resources, and a minimum of changes in direction.

Soybean (*Glycine max*) is an important and valuable field crop. Thus, a continuing goal of soybean breeders is to develop stable, high yielding soybean varieties that are agronomically sound. The reasons for this goal are to maximize the amount of grain produced on the land used and to supply food for both animals and humans. To accomplish this goal, the soybean breeder must select and develop soybean plants that have the traits that result in superior varieties.

The soybean is the world's leading source of vegetable oil and protein meal. The oil extracted from soybeans is used for cooking oil, margarine, and salad dressings. Soybean oil is composed of saturated, monounsaturated, and polyunsaturated fatty acids. It has a typical composition of 11% palmitic, 4% stearic, 25% oleic, 50% linoleic, and 9% linolenic fatty acid content ("Economic Implications of Modified Soybean Traits Summary Report", Iowa Soybean Promotion Board & American Soybean Association Special Report 92S, May 1990). Changes in fatty acid composition for improved oxidative stability and nutrition are also important traits.

Industrial uses for processed soybean oil include ingredients for paints, plastics, fibers, detergents, cosmetics, and lubricants. Soybean oil may be split, inter-esterified, sulfurized, epoxidized, polymerized, ethoxylated, or cleaved. Designing and producing soybean oil derivatives with improved functionality, oliochemistry, is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

Soybean is also used as a food source for both animals and humans. Soybean is widely used as a source of protein for animal feeds for poultry, swine, and cattle. During processing of whole soybeans, the fibrous hull is removed and the oil is extracted. The remaining soybean meal is a combination of carbohydrates and approximately 50% protein.

For human consumption soybean meal is made into soybean flour which is processed to protein concentrates used for meat extenders or specialty pet foods. Production of edible protein ingredients from soybean offers a healthy, less expensive replacement for animal protein in meats and dairy products.

SUMMARY

A novel soybean variety, designated XB33H12 is provided. Also provided are the seeds of soybean variety XB33H12, cells from soybean variety XB33H12, plants of soybean XB33H12, and plant parts of soybean variety XB33H12. Methods provided include producing a soybean plant by crossing soybean variety XB33H12 with another soybean plant, methods for introgressing a transgenic, a mutant trait, and/or a native trait into soybean variety XB33H12, methods for producing other soybean varieties or plant parts derived from soybean variety XB33H12, and methods of characterizing soybean variety XB33H12. Soybean seed, cells, plants, germplasm, breeding lines, varieties, and plant parts produced by these methods and/or derived from soybean variety XB33H12 are further provided.

Definitions

Certain definitions used in the specification are provided below. Also in the examples which follow, a number of terms are used. In order to provide a clear and consistent understanding of the specification and claims, the following definitions are provided:

AERBLT=AWB=AERIAL WEB BLIGHT. Aerial web blight is caused by the fungus *Rhizoctonia solani*, which can also cause seedling blight and root rot of soybeans. Stems, flowers, pods, petioles, and leaves are susceptible to formation of lesions. Tolerance to Aerial Web Blight is rated on a scale of 1 to 9, relative to known checks, with a score of 1 being susceptible, and a score of 9 being tolerant. Preliminary scores are reported as double digits, for example '55' indicates a preliminary score of 5 on the scale of 1 to 9.

ALLELE. Any of one or more alternative forms of a genetic sequence. In a diploid cell or organism, the two alleles of a given sequence typically occupy corresponding loci on a pair of homologous chromosomes.

ANTHESIS. The time of a flower's opening.

ANTHRACNOSE. Anthracnose is a fungal disease commonly caused by *Colletotrichum truncatum*, and in some cases other *Colletotrichum* species may be involved. The fungus produces crowded, black acervuli on infected tissues. These dark bodies typically look like pin cushions on the tissue surface when viewed under magnification. The most common symptoms are brown, irregularly shaped spots on stem, pods and petioles. Resistance is visually scored on a range from 1 to 9 comparing all genotypes in a given experiment. A score of 9 indicates that there is no infection (resistance). Preliminary scores are reported as double digits, for example '55' indicates a preliminary score of 5 on the scale of 1 to 9.

APHID ANTIBIOSIS. Aphid antibiosis is the ability of a variety to reduce the survival, growth, or reproduction of aphids that feed on it. Screening scores are based on the ability of the plant to decrease the rate of aphid reproduction. Plants are compared to resistant and susceptible check plants grown in the same experiment. Scores of 1=susceptible, 3=below average, 5=average, 7=above average, and 9=exceptional tolerance. Preliminary scores are reported as double digits, for example '55' indicates a preliminary score of 5 on the scale of 1 to 9.

APHID ANTIXENOSIS. Aphid antixenosis is a property of a variety to reduce the feeding of aphids upon the plant, this is also known as nonpreference. Screening scores are based on the ability of the plant to decrease the rate of aphid reproduction. Plants are compared to resistant and susceptible check plants grown in the same experiment. Scores of 1=susceptible plants covered with aphids, plants may show severe damage such as stunting and/or necrosis, equivalent or worse when compared to susceptible check, 3=below average, plants show major damage such as stunting and/or foliar necrosis, 5=moderately susceptible, 7=above average, about 50 aphids on the plant, plant does not exhibit signs of plant stress, and 9=exceptional tolerance, very few aphids on the plant, equivalent or better when compared to a resistant check. Preliminary scores are reported as double digits, for example '55' indicates a preliminary score of 5 on the scale of 1 to 9.

BACKCROSSING. Process in which a breeder crosses a donor parent variety possessing a desired trait or traits to a recurrent parent variety (which is agronomically superior but lacks the desired level or presence of one or more traits) and then crosses the resultant progeny back to the recurrent parent one or more times. Backcrossing can be used to introduce one or more desired traits from one genetic background into another background that is lacking the desired traits.

BREEDING. The genetic manipulation of living organisms, including application of one or more agricultural and/or biotechnological tools, methods and/or processes to create useful new distinct varieties.

BU/A=Bushels per Acre. The seed yield in bushels/acre is the actual yield of the grain at harvest.

BROWN STEM ROT=BSR=Brown Stem Rot Tolerance. This is a visual disease score from 1 to 9 comparing all genotypes in a given test. The score is based on symptoms on leaves and/or stems such as yellowing, necrosis, and on inner stem rotting caused by *Phialophora gregata*. A score of 1 indicates severe symptoms of leaf yellowing and necrosis. Increasing visual scores from 2 to 8 indicate additional levels of tolerance, while a score of 9 indicates no symptoms. Preliminary scores are reported as double digits, for example '55' indicates a preliminary score of 5 on the scale of 1 to 9.

BSRLF=Brown Stem Rot disease rating based solely on leaf disease symptoms. This is a visual disease score from 1 to 9 comparing all genotypes in a given test. A score of 1 indicates severe leaf yellowing and necrosis. Increasing visual scores from 2 to 8 indicate additional levels of tolerance, while a score of 9 indicates no leaf symptoms. Preliminary scores are reported as double digits, for example '55' indicates a preliminary score of 5 on the scale of 1 to 9.

BSRSTM=Brown Stem Rot disease rating based solely on stem disease symptoms. This is a visual disease score from 1 to 9 comparing all genotypes in a given test. A score of 1 indicates severe necrosis on the inner stem tissues. Increasing visual scores from 2 to 8 indicate additional levels of tolerance, while a score of 9 indicates no inner stem symptoms. Preliminary scores are reported as double digits, for example '55' indicates a preliminary score of 5 on the scale of 1 to 9.

CELL. Cell as used herein includes a plant cell, whether isolated, in tissue culture, or incorporated in a plant or plant part.

CERK=*CERCOSPORA* TOLERANCE. A fungal disease caused by *Cercospora kukuchii* which can be identified by symptoms including one or more of mottled reddish-purple discoloration of the uppermost leaves of the soybean plant, mottled discoloration of leaf petioles, mottled discoloration of pods, and/or purple discoloration of the seed coat. Infected seed, having a purple discoloration, is commonly referred to as purple seed stain. For the multiple expressions of this disease, plants or plant parts are visually scored from 1 to 9 relative to picture diagrams for each trait. A score of 1 indicates severity of expression, while a score of 9 indicates no symptoms. Preliminary scores are reported as double digits, for example '55' indicates a preliminary score of 5 on the scale of 1 to 9.

CRDC=CHARCOAL ROT DROUGHT COMPLEX. A fungal disease caused by *Macrophomina phaseolina* that is enhanced by hot and dry conditions, especially during reproductive growth stages. Tolerance score is based on field observations of the comparative ability to tolerate drought and limit losses from charcoal rot infection among various soybean varieties. A score of 1 indicates severe charcoal rot on the roots and dark microsclerotia on the lower stem causing significant plant death. Increasing visual scores from 2 to 8 indicate additional levels of tolerance, while a score of 9 indicates no lower stem and/or root rot and no visual symptoms. Preliminary scores are reported as double digits, for example '55' indicates a preliminary score of 5 on the scale of 1 to 9.

CHLORIDE SALT TOLERANCE. This is a measure of the chloride salt concentration in seedling plant tissue, arrayed on a scale based on checks, and scores applied from 1 to 9. The higher the score the lower the concentration of chloride salts in the tissue measured. Preliminary scores are reported as double digits, for example '55' indicates a preliminary score of 5 on the scale of 1 to 9.

CW=Canopy Width. This is a visual observation of the canopy width which is scored from 1 to 9 comparing all genotypes in a given test. A score of 1=very narrow, while a score of 9=very bushy.

CNKST=SOUTHERN STEM CANKER TOLERANCE. This is a visual disease score from 1 to 9 comparing genotypes to standard checks chosen to array differences. The score is based upon field reaction to the disease. The causative agent is *Diaporthe phaseolorum* var. *meridionalis* (Southern Stem Canker), which tends to impact southern geographic regions. A score of 1 indicates susceptibility to the disease, whereas a score of 9 indicates the line is resistant to the disease. Preliminary scores are reported as double digits, for example '55' indicates a preliminary score of 5 on the scale of 1 to 9.

CNKSG=SOUTHERN STEM CANKER GENETIC. This is a visual disease score from 1 to 9 comparing genotypes to standard checks chosen to array differences. The score is based upon toothpick bioassay in (1) field or shade tent bioassays or (2) controlled environmental chambers, and is based on genetics that infers resistance or susceptibility to Southern Stem Canker. *Diaporthe phaseollorum* var. *meridionalis* is the causative agent. A score of 1 indicates severe stem canker lesions, relative to known susceptible check varieties, whereas a score of 9 indicates no meaningful disease symptoms, consistent with known resistant check varieties. Preliminary scores are reported as double digits, for example '99' indicates a preliminary score of 9 on the scale of 1 to 9.

COTYLEDON. A cotyledon is a type of seed leaf. The cotyledon contains the food storage tissues of the seed.

CROSS-POLLINATION. Fertilization by the union of two gametes from different plants.

DIPLOID. A cell or organism having two sets of chromosomes.

DM=DOWNY MILDEW. A fungal disease caused by *Peronospora manshurica* in soybean. Symptoms first appear on leaves, which can spread to pods without obvious external symptoms, and further spread to seed. Infected seed may have a dull white appearance. The tolerance score is based on observations of symptoms on the leaves of plants regarding leaf damage and/or level of infection. On a scale of 1 to 9, a score of 1 indicates severe symptoms, whereas a score of 9 indicates no disease symptoms. Preliminary scores are reported as double digits, for example '55' indicates a preliminary score of 5 on the scale of 1 to 9.

ELITE VARIETY. A variety that is sufficiently homozygous and homogeneous to be used for commercial grain production. An elite variety may also be used in further breeding.

EMBRYO. The embryo is the small plant contained within a mature seed.

EMGSC=Emergence Score=Field Emergence. A score based upon speed and strength of emergence at sub-optimal conditions. Rating is done at the unifoliate to first trifoliate stages of growth. A score using a 1 to 9 scale is given, with 1 being the poorest and 9 the best. Scores of 1, 2, and 3=degrees of unacceptable stands; slow growth and poor plant health. Scores of 4, 5, 6=degrees of less than optimal stands; moderate growth and plant health. Scores of 7, 8, 9=degrees of optimal stands; vigorous growth and plant health.

FEC=Iron-deficiency Chlorosis. Plants are scored 1 to 9 based on visual observations. A score of 1 indicates the plants are dead or dying from iron-deficiency chlorosis, a score of 5 means plants have intermediate health with some leaf yellowing, and a score of 9 means no stunting of the plants or yellowing of the leaves. Preliminary scores are reported as double digits, for example '55' indicates a preliminary score of 5 on the scale of 1 to 9.

FEY=FROGEYE LEAF SPOT. This is a visual fungal disease score from 1 to 9 comparing all genotypes in a given trial to known resistant and susceptible checks in the trial. The score is based upon the number and size of leaf lesions. A score of 1 indicates severe leaf necrosis lesions, whereas a score of 9 indicates no lesions. Preliminary scores are reported as double digits, for example '55' indicates a preliminary score of 5 on the scale of 1 to 9.

FLOWER COLOR. Data values include: P=purple and W=white.

GENE SILENCING. The interruption or suppression of the expression of a nucleic acid sequence at the level of transcription or translation.

GENOTYPE. Refers to the genetic constitution of a cell or organism.

PLANT HABIT. This refers to the physical appearance of a plant. It can be determinate (Det), semi-determinate, intermediate, or indeterminate (Ind). In soybeans, indeterminate varieties are those in which stem growth is not limited by formation of a reproductive structure (i.e., flowers, pods and seeds) and hence growth continues throughout flowering and during part of pod filling. The main stem will develop and set pods over a prolonged period under favorable conditions. In soybeans, determinate varieties are those in which stem growth ceases at flowering time. Most flowers develop simultaneously, and most pods fill at approximately the same time. The terms semi-determinate and intermediate are also used to describe plant habit and are defined in Bernard, R. L. (1972) "Two genes affecting stem termination in soybeans." Crop Science 12:235-239; Woodworth, C. M. (1932) "Genetics and breeding in the improvement of the soybean." Bull. Agric. Exp. Stn. (Illinois) 384:297-404; and Woodworth, C. M. (1933) "Genetics of the Soybean." J. Am. Soc. Agron. 25:36-51.

HAPLOID. A cell or organism having one set of the two sets of chromosomes in a diploid cell or organism.

HERBRES=Herbicide Resistance. This indicates that the plant is more tolerant to the herbicide shown than the level of herbicide tolerance exhibited by wild type plants. A designation of 'Gly' indicates tolerance to glyphosate, and a designation of 'STS' indicates tolerance to sulfonylurea herbicides.

HGT=Plant Height. Plant height is taken from the top of the soil to the top pod of the plant and is measured in inches.

HILUM. This refers to the scar left on the seed which marks the place where the seed was attached to the pod prior to harvest. Hila Color data values include: BR=brown; TN=tan; Y=yellow; BL=black; IB=Imperfect Black; BF=buff. Tan hila may also be designated as imperfect yellow (IY).

HLC=HO=High Oleic. Oil with seventy percent or more oleic acid is classified as high oleic oil. Oleic acid is one of the five most abundant fatty acids in soybean seeds. It is measured by gas chromatography and is reported as a percent of the total oil content.

HYPLSC=Hypocotyl length=Hypocotyl elongation. This score indicates the ability of the seed to emerge when planted 3" deep in sand pots and with a controlled temperature of 25° C. The number of plants that emerge each day are counted. Based on this data, each genotype is given a score from 1 to 9 based on its rate of emergence and the percent of emergence. A score of 1 indicates a very poor rate and percent of emergence, an intermediate score of 5 indicates average ratings, and a score of 9 indicates an excellent rate and percent of emergence. Preliminary scores are reported as double digits, for example '55' indicates a preliminary score of 5 on the scale of 1 to 9.

HYPOCOTYL. A hypocotyl is the portion of an embryo or seedling between the cotyledons and the root.

LDGSEV=Lodging Resistance=Harvest Standability. Lodging is rated on a scale of 1 to 9. A score of 1 indicates plants that are lying on the ground, a score of 5 indicates plants are leaning at a 45° angle in relation to the ground, and a score of 9 indicates erect plants. Preliminary scores are reported as double digits, for example '55' indicates a preliminary score of 5 on the scale of 1 to 9.

LEAFLETS. These are parts of the plant shoot involved in the manufacture of food for the plant by the process of photosynthesis.

LINKAGE. Refers to a phenomenon wherein alleles on the same chromosome tend to segregate together more often than expected by chance if their transmission was independent.

LINKAGE DISEQUILIBRIUM. Refers to a phenomenon wherein alleles tend to remain together in linkage groups when segregating from parents to offspring, with a greater frequency than expected from their individual frequencies.

LLC=Oil with three percent or less linolenic acid is classified as low linolenic oil. Linolenic acid is one of the five most abundant fatty acids in soybean seeds. It is measured by gas chromatography and is reported as a percent of the total oil content.

LLE=Linoleic Acid Percent. Linoleic acid is one of the five most abundant fatty acids in soybean seeds. It is measured by gas chromatography and is reported as a percent of the total oil content.

LLN=Linolenic Acid Percent. Linolenic acid is one of the five most abundant fatty acids in soybean seeds. It is measured by gas chromatography and is reported as a percent of the total oil content.

LOCUS. A defined segment of DNA.

LOCUS CONVERSION. Refers to seeds, plants, and/or parts thereof developed by backcrossing wherein essentially all of the desired morphological and physiological characteristics of a variety are recovered in addition to at least one locus which has been transferred into the variety. The locus can be a native locus, a transgenic locus, or a combination thereof.

PRM=PRMMAT=Predicted Relative Maturity=RM=Relative Maturity.

Soybean maturities are divided into relative maturity groups (denoted as 000, 00, 0, I, II, III, IV, V, VI, VII, VIII, IX, X, or 000, 00, 0, 1, 2, 3, 4, 5, 6, 7, 8, 9, 10). Within a maturity group are sub-groups. A sub-group is a tenth of a relative maturity group (for example 1.3 would indicate a group 1 and subgroup 3). Within narrow comparisons, the difference of a tenth of a relative maturity group equates very roughly to a day difference in maturity at harvest.

MAT ABS=ABSOLUTE MATURITY. This term is defined as the length of time from planting to complete physiological development (maturity). The period from planting until maturity is reached is measured in days, usually in comparison to one or more standard varieties. Plants are considered mature when 95% of the pods have reached their mature color.

MATURITY GROUP. This refers to an agreed-on industry division of groups of varieties, based on the zones in which they are adapted primarily according to day length or latitude. They consist of very long day length varieties (Groups 000, 00, 0), and extend to very short day length varieties (Groups VII, VIII, IX, X).

NARROW ROWS. Term indicates 7" and 15" row spacing.

NEI DISTANCE. A quantitative measure of percent similarity between two lines. Nei's distance between lines A and B can be defined as 1−((2*number alleles in common)/(number alleles in A+number alleles in B)). For example, if lines A and B are the same for 95 out of 100 alleles, the Nei distance would be 0.05. If lines A and B are the same for 98 out of 100 alleles, the Nei distance would be 0.02. Free software for calculating Nei distance is available on the internet at multiple locations such as, e.g., evolution.genetics.washington.edu/phylip.html. See Nei & Li (1979) Proc Natl Acad Sci USA 76:5269-5273, which is incorporated by reference for this purpose.

NUCLEIC ACID. An acidic, chain-like biological macromolecule consisting of multiple repeat units of phosphoric acid, sugar, and purine and pyrimidine bases.

OIL=OIL PERCENT=OIL (%). Soybean seeds contain a considerable amount of oil. Oil is measured by NIR spectrophotometry and is reported as a percentage basis.

OIL/MEAL TYPE. Designates varieties specially developed with the following oil traits: HLC=High Oleic oil (≥70% oleic contect); LLC=Low Linolenic (≤3% linolenic content); ULC=Ultra Low Linolenic oil (≤1% linolenic oil content).

OLC=OLEIC ACID PERCENT. Oleic acid is one of the five most abundant fatty acids in soybean seeds. It is measured by gas chromatography and is reported as a percent of the total oil content.

PEDIGREE DISTANCE. Relationship among generations based on their ancestral links as evidenced in pedigrees. May be measured by the distance of the pedigree from a given starting point in the ancestry.

PERCENT IDENTITY. Percent identity as used herein refers to the comparison of the homozygous alleles of two soybean varieties. Percent identity is determined by comparing a statistically significant number of the homozygous alleles of two developed varieties. For example, a percent identity of 90% between soybean variety 1 and soybean variety 2 means that the two varieties have the same allele at 90% of the loci used in the comparison.

PERCENT SIMILARITY. Percent similarity as used herein refers to the comparison of the homozygous alleles of a soybean variety such as XB33H12 with another plant, and if the homozygous allele of XB33H12 matches at least one of the alleles from the other plant, then they are scored as similar. Percent similarity is determined by comparing a statistically significant number of loci and recording the number of loci with similar alleles as a percentage. A percent similarity of 90% between XB33H12 and another plant means that XB33H12 matches at least one of the alleles of the other plant at 90% of the loci used in the comparison.

PLANT. As used herein, the term "plant" includes reference to an immature or mature whole plant, including a plant from which seed or grain or anthers have been removed. Any seed or embryo that will produce the plant is also considered to be the plant.

PLANT PARTS. As used herein, the term "plant parts" includes leaves, stems, roots, root tips, anthers, seed, grain, embryos, pollen, ovules, flowers, cotyledon, hypocotyl, pod, flower, shoot, stalk, tissue, tissue cultures, cells and the like.

PLM or PALMITIC ACID PERCENT. Palmitic acid is one of the five most abundant fatty acids in soybean seeds. It is measured by gas chromatography and is reported as a percent of the total oil content.

PMG infested soils. Soils containing *Phytophthora sojae*.

POD. This refers to the fruit of a soybean plant. It consists of the hull or shell (pericarp) and the soybean seeds. Pod Color data values include: BR=brown; TN=tan.

POWDERY MILDEW. Powdery Mildew is caused by a fungus, *Microsphaera diffusa*. Tolerance to Powdery Mildew is rated on a scale of 1 to 9, with a score of 1 being very susceptible ranging up to a score of 9 being tolerant. Preliminary scores are reported as double digits, for example '55' indicates a preliminary score of 5 on the scale of 1 to 9.

PRT or *PHYTOPHTHORA* FIELD TOLERANCE. Tolerance to *Phytophthora* root rot is rated on a scale of 1 to 9, with a score of 1 indicating the plants have no tolerance to *Phytophthora*, ranging to a score of 9 being the best or highest tolerance. PRTLAB indicates the tolerance was scored using plants in lab assay experiments. Preliminary scores are reported as double digits, for example '55' indicates a preliminary score of 5 on the scale of 1 to 9.

*PHYTOPHTHORA* RESISTANCE GENE (Rps). Various *Phytophthora* resistance genes are known and include but are not limited to: Rps1-a=resistance to races 1-2, 10-11, 13-8, 24; Rps1-c=resistance to races 1-3, 6-11, 13, 15, 17, 21, 23, 24, 26, 28-30, 32, 34, 36; Rps1-k=resistance to races 1-11, 13-15, 17, 18, 21-24, 26, 36, 37; Rps3-a=resistance to races 1-5, 8, 9, 11, 13, 14, 16, 18, 23, 25, 28, 29, 31-35, 39-41, 43-45, 47-52, 54; Rps3-c=resistance to races 1-4, 10-16, 18-36, 38-54; Rps6=resistance to races 1-4, 10, 12, 14-16, 18-21, 25, 28, 33-35; and, Rps8=resistance to races 1-5, 9, 13-15, 21, 25, 29, 32. As reported in Table 1 "-" or " " indicates that a specific gene for resistance has not been identified to date.

PRO=PROTN=PROTN (%)=PROTEIN PERCENT. Soybean seeds contain a considerable amount of protein. Protein is generally measured by NIR spectrophotometry, and is reported as a percent on a dry weight basis.

PUBESCENCE. This refers to a covering of very fine hairs closely arranged on the leaves, stems and pods of the soybean plant. Pubescence color data values include: L=Light Tawny; T=Tawny; G=Gray.

R160=Palmitic Acid percentage. Percentage of palmitic acid as determined using methods described in Reske et al. (1997) "Triacylglycerol Composition and Structure in Genetically Modified Sunflower and Soybean Oils" JAOCS 74:989-998, which is incorporated by reference for this purpose.

R180=Stearic acid percentage. Percentage of Stearic acid as determined using methods described in Reske et al. (1997) JAOCS 74:989-998, which is incorporated by reference for this purpose.

R181=Oleic acid percentage. Percentage of oleic acid as determined using methods described in Reske et al. (1997) JAOCS 74:989-998, which is incorporated by reference for this purpose.

R182=Linoleic acid percentage. Percentage of linoleic acid as determined using methods described in Reske et al. (1997) JAOCS 74:989-998, which is incorporated by reference for this purpose.

R183=Linolenic acid percentage. Percentage of linolenic acid as determined using methods described in Reske et al. (1997) JAOCS 74:989-998, which is incorporated by reference for this purpose.

RESISTANCE. As used herein, resistance is synonymous with tolerance and is used to describe the ability of a plant to withstand exposure to an insect, disease, herbicide, environmental stress, or other condition. A resistant plant variety will be able to better withstand the insect, disease pathogen, herbicide, environmental stress, or other condition as compared to a non-resistant or wild-type variety.

RKI=SOUTHERN ROOT-KNOT NEMATODE. Southern root knot nematode, *Meloidogyne incognita*, is a plant parasite that can cause major damage to roots, reducing yield potential. Severity is visually scored on roots in a range from 1 to 9 comparing all genotypes in a given experiment to known resistant and susceptible checks. The score is determined by visually scoring the roots for presence or absence of galling in a controlled chamber bioassay. A score of 1 indicates severe galling of the root system which can cause premature death from decomposition of the root system (susceptible). A score of 9 indicates that there is little to no galling of the roots (resistant). Preliminary scores are reported as double digits, for example '55' indicates a preliminary score of 5 on the scale of 1 to 9.

RKA=PEANUT ROOT-KNOT NEMATODE. Peanut root knot nematode, *Meloidogyne arenaria*, is a plant parasite that can cause major damage to roots, reducing yield potential. Severity is visually scored on roots in a range from 1 to 9 comparing all genotypes in a given experiment to known resistant and susceptible checks. The score is determined by visually scoring the roots for presence or absence of galling in a controlled chamber bioassay. A score of 1 indicates severe galling of the root system which can cause pre-mature death from decomposition of the root system (susceptible). A score of 9 indicates that there is little to no galling of the roots (resistant). Preliminary scores are reported as double digits, for example '55' indicates a preliminary score of 5 on the scale of 1 to 9.

RKJ=*JAVANICA* ROOT-KNOT NEMATODE. *Javonica* root knot nematode, *Meloidogyne javonica*, is a plant parasite that can cause major damage to roots, reducing yield potential. Severity is visually scored on roots in a range from 1 to 9 comparing all genotypes in a given experiment to known resistant and susceptible checks. The score is determined by visually scoring the roots for presence or absence of galling in a controlled chamber bioassay. A score of 1 indicates severe galling of the root system which can cause premature death from decomposition of the root system (susceptible). A score of 9 indicates that there is little to no galling of the roots (resistant). Preliminary scores are reported as double digits, for example '55' indicates a preliminary score of 5 on the scale of 1 to 9.

SCN=SOYBEAN CYST NEMATODE RESISTANCE=Cyst Nematode Resistance. The score is based on resistance to a particular race of soybean cyst nematode (*Heterodera glycines*), such as race 1, 2, 3, 5 or 14. Scores are from 1 to 9 and indicate visual observations of resistance as compared to other genotypes in the test. A score of 1 indicates nematodes are able to infect the plant and cause yield loss, while a score of 9 indicates SCN resistance. Preliminary scores are reported as double digits, for example '55' indicates a preliminary score of 5 on the scale of 1 to 9.

SCN Resistance Source. There are three typical sources of genetic resistance to SCN: PI88788, PI548402 (also known as Peking), and PI437654 (also known as Hartwig).

SCN infected soils. Soils containing soybean cyst nematode.

SD VIG or Seedling Vigor. The score is based on the speed of emergence of the plants within a plot relative to other plots within an experiment. A score of 1 indicates no plants have expanded first leaves, while a score of 9 indicates that 90% of plants growing have expanded first leaves.

SDS or SUDDEN DEATH SYNDROME. SDS is caused by the fungal pathogen formerly known as *Fusarium solani* f.sp. glycines, which is currently known as *Fusarium virguliforme* (see, e.g., Aoki et al. (2003) Mycologia 95:660-684). Tolerance to Sudden Death Syndrome is rated on a scale of 1 to 9, with a score of 1 being very susceptible ranging up to a score of 9 being tolerant. Preliminary scores are reported as double digits, for example '55' indicates a preliminary score of 5 on the scale of 1 to 9.

SEED COAT LUSTER. Data values include D=dull; S=shiny.

SEED SIZE SCORE. This is a measure of the seed size from 1 to 9. The higher the score, the smaller the seed size measured. Preliminary scores are reported as double digits, for example '55' indicates a preliminary score of 5 on the scale of 1 to 9.

*SEPTORIA* LEAF SPOT. *Septoria* Leaf Spot, also known as Brown Spot, is caused by the fungus *Septoria* glycines. Symptoms can occur as early as V2 on lower leaves, and may move up the plant affecting leaves as well as stems and pods in plants approaching maturity. Symptoms include irregular dark brown spots on upper and lower leaf surfaces, or the stems or pods. Infected leaves may yellow or brown and drop early. Tolerance to *Septoria* Leaf Spot is rated on a scale of 1 to 9, with a score of 1 being very susceptible ranging up to a score of 9 being tolerant. Preliminary scores are reported as double digits, for example '55' indicates a preliminary score of 5 on the scale of 1 to 9.

SPLB=S/LB=Seeds per Pound. Soybean seeds vary in seed size, therefore, the number of seeds required to make up one pound also varies. This affects the pounds of seed required to plant a given area, and can also impact end uses.

SHATTR or Shattering. This refers to the amount of pod dehiscence prior to harvest. Pod dehiscence involves seeds falling from the pods to the soil. This is a visual score from 1 to 9 comparing all genotypes within a given test. A score of 1 indicates 100% of the pods are opened, while a score of 9 means pods have not opened and no seeds have fallen out.

SHOOTS. These are a portion of the body of the plant. They consist of stems, petioles and leaves.

STC or Stearic Acid Percent. Stearic acid is one of the five most abundant fatty acids in soybean seeds. It is measured by gas chromatography and is reported as a percent of the total oil content.

SUBLINE. Although XB33H12 contains substantially fixed genetics, and is phenotypically uniform and with no off-types expected, there still remains a small proportion of segregating loci either within individuals or within the population as a whole. The segregating loci both within any individual plant and/or the population can be used to extract unique varieties (sublines) with similar phenotype but improved agronomics.

TARGET SPOT. This is a fungal disease caused by *Corynespora cassiicola*. Symptoms usually consist of roughly circular, necrotic leaf lesions from minute to 11 mm in diameter, though typically approximately 4 to 5 mm in diameter, and with a yellow margin. Large lesions occasionally exhibit a zonate pattern associated with this disease. Tolerance to target spot is scored from 1 to 9 by visually comparing all genotypes in a given test. A score of 1 indicates complete death of the experimental unit while a score of 9 indicates no symptoms. Preliminary scores are reported as double digits, for example '55' indicates a preliminary score of 5 on the scale of 1 to 9.

WHMD or WHITE MOLD TOLERANCE. This is a fungal disease caused by *Sclerotinia sclerotiorum* that creates mycelial growth and death of plants. Tolerance to white mold is scored from 1 to 9 by visually comparing all genotypes in a given test. A score of 1 indicates complete death of the experimental unit while a score of 9 indicates no symptoms. Preliminary scores are reported as double digits, for example '55' indicates a preliminary score of 5 on the scale of 1 to 9.

VARIETY. A substantially homozygous soybean line and minor modifications thereof that retains the overall genetics of the soybean line including but not limited to a subline, a locus conversion, a mutation, a transgenic, or a somaclonal variant. Variety includes seeds, plants, plant parts, and/or seed parts of the instant soybean line.

HIGH YIELD ENVIRONMENTS. Areas which lack normal stress, typically having sufficient rainfall, water drainage, low disease pressure, and low weed pressure.

TOUGH ENVIRONMENTS. Areas which have stress challenges, opposite of a high yield environment.

DETAILED DESCRIPTION

Soybean variety XB33H12 has shown uniformity and stability for all traits, as described in the following variety description information. Soybean variety XB33H12 was developed from a cross of 93M61 with RJS34001. Variety XB33H12 is an F3-derived line which was advanced to the F3 generation by modified single-seed descent. It has been self-pollinated a sufficient number of generations, with careful attention to uniformity of plant type to ensure a sufficient level of homozygosity and phenotypic stability. The variety has been increased with continued observation for uniformity. No variant traits have been observed or are expected.

A variety description of soybean variety XB33H12 is provided in Table 1.

Traits reported are average values for all locations and years or samples measured. Preliminary scores are reported as double digits, for example '55' indicates a preliminary score of 5 on the scale of 1 to 9.

Soybean variety XB33H12, being substantially homozygous, can be reproduced by planting seeds of the variety, growing the resulting soybean plants under self-pollinating or sib-pollinating conditions, and harvesting the resulting seed, using techniques familiar to the agricultural arts. Development of soybean variety XB33H12 is shown in the breeding history summary in Table 4.

Performance Examples of XB33H12

As shown in Table 2, the traits and characteristics of soybean variety XB33H12 are given in paired comparisons with other varieties. Traits reported are mean values for all locations and years where paired comparison data was obtained.

Genetic Marker Profile

In addition to phenotypic observations, a plant can also be identified by its genotype. The genotype of a plant can be characterized through a genetic marker profile which can identify plants of the same variety or a related variety, or which can be used to determine or validate a pedigree. Genetic marker profiles can be obtained by techniques such as restriction fragment length polymorphisms (RFLPs), randomly amplified polymorphic DNAs (RAPDs), arbitrarily primed polymerase chain reaction (AP-PCR), DNA amplification fingerprinting (DAF), sequence characterized amplified regions (SCARs), amplified fragment length polymorphisms (AFLPs), simple sequence repeats (SSRs) also referred to as microsatellites, or single nucleotide polymorphisms (SNPs). For example, see Cregan et al. (1999) "An Integrated Genetic Linkage Map of the Soybean Genome" Crop Science 39:1464-1490, and Berry et al. (2003) "Assessing Probability of Ancestry Using Simple Sequence Repeat Profiles: Applications to Maize Inbred Lines and Soybean Varieties" Genetics 165:331-342, each of which are incorporated by reference herein in their entirety.

Methods of characterizing soybean variety XB33H12, or a variety comprising the morphological and physiological characteristics of soybean variety XB33H12, are provided. In one example a method comprising isolating nucleic acids from a plant, a plant part, or a seed of soybean variety XB33H12, analyzing said nucleic acids to produce data, and recording the data for XB33H12 is provided. In some examples the data comprises one of more of a nucleic acid sequence, a genetic profile, a molecular profile, a marker profile, a haplotype, or any combination thereof. In some examples, the data is recorded on a computer readable medium. In other examples, the methods may further comprise using the data for soybean crossing, selection and/or advancement decisions. Crossing includes any type of plant breeding crossing method, including but not limited to outcrossing, selfing, backcrossing, locus conversion, introgression and the like.

In some examples, one or more markers are used to characterize and/or evaluate a soybean variety. Particular markers used for these purposes are not limited to any particular set of markers, but are envisioned to include any type of marker and marker profile which provides a means of distinguishing varieties. For example, one set of publicly available markers which could be used to screen and identify variety XB33H12 is disclosed in Table 3. In another example, one method of comparison is to use only homozygous loci for XB33H12.

Primers and PCR protocols for assaying these and other markers are disclosed in Soybase (sponsored by the USDA Agricultural Research Service and Iowa State University) located on the world wide web at 129.186.26.94/SSR.html. In addition to being used for identification of soybean variety XB33H12, and plant parts and plant cells of variety XB33H12, the genetic profile may be used to identify a soybean plant produced through the use of XB33H12 or to verify a pedigree for progeny plants produced through the use of XB33H12. The genetic marker profile is also useful in breeding and developing backcross conversions.

The present invention comprises a soybean plant characterized by molecular and physiological data obtained from the representative sample of said variety deposited with the American Type Culture Collection (ATCC). Thus, plants, seeds, or parts thereof, having all or substantially all of the physiological and morphological characteristics of soybean variety XB33H12 are provided. Further provided is a soybean plant formed by the combination of the disclosed soybean plant or plant cell with another soybean plant or cell and comprising the homozygous alleles of the variety. A soybean plant comprising all of the physiological and morphological characteristics of soybean variety XB33H12 can be combined with another soybean plant in a soybean breeding program. In some examples the other soybean plant comprises all of the physiological and morphological characteristics of soybean variety XB33H12.

In some examples, a plant, a plant part, or a seed of soybean variety XB33H12 is characterized by producing a molecular profile. A molecular profile includes but is not limited to one or more genotypic and/or phenotypic profile(s). A genotypic profile includes but is not limited to a marker profile, such as a genetic map, a linkage map, a trait marker profile, a SNP profile, an SSR profile, a genome-wide marker profile, a haplotype, and the like. A molecular profile may also be a nucleic acid sequence profile, and/or a physical map. A phenotypic profile includes but is not limited to a protein expression profile, a metabolic profile, an mRNA expression profile, and the like.

Means of performing genetic marker profiles using SSR polymorphisms are well known in the art. A marker system based on SSRs can be highly informative in linkage analysis relative to other marker systems in that multiple alleles may be present. Another advantage of this type of marker is that, through use of flanking primers, detection of SSRs can be achieved, for example, by using the polymerase chain reaction (PCR), thereby eliminating the need for labor-intensive Southern hybridization. PCR detection is done using two oligonucleotide primers flanking the polymorphic segment of repetitive DNA to amplify the SSR region.

Following amplification, markers can be scored by electrophoresis of the amplification products. Scoring of marker genotype is based on the size of the amplified fragment, which correlates to the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

Primers used are publicly available and may be found in Soybase or Cregan (1999 Crop Science 39:1464-1490). See also, WO 99/31964 "Nucleotide Polymorphisms in Soybean", U.S. Pat. No. 6,162,967 "Positional Cloning of Soybean Cyst Nematode Resistance Genes", and U.S. Pat. No. 7,288,386 "Soybean Sudden Death Syndrome Resistant Soybeans and Methods of Breeding and Identifying Resistant Plants", the disclosures of which are incorporated herein by reference.

The SSR profile of soybean plant XB33H12 can be used to identify plants comprising XB33H12 as a parent, since such plants will comprise the same homozygous alleles as XB33H12. Because the soybean variety is essentially homozygous at all relevant loci, most loci should have only one type of allele present. In contrast, a genetic marker profile of an F1 progeny should be the sum of those parents, e.g., if one parent was homozygous for allele X at a particular locus, and the other parent homozygous for allele Y at that locus, then the F1 progeny will be XY (heterozygous) at that locus. Subsequent generations of progeny produced by selection and breeding are expected to be of genotype XX (homozygous), YY (homozygous), or XY (heterozygous) for that locus position. When the F1 plant is selfed or sibbed for successive filial generations, the locus should be either X or Y for that position.

In addition, plants and plant parts substantially benefiting from the use of XB33H12 in their development, such as XB33H12 comprising a backcross conversion, transgene, or genetic sterility factor, may be identified by having a molecular marker profile with a high percent identity to XB33H12. Such a percent identity might be 90%, 91%, 92%, 93%, 94%, 95%, 96%, 97%, 98%, 99%, 99.5%, or 99.9% identical to XB33H12.

The SSR profile of variety XB33H12 also can be used to identify essentially derived varieties and other progeny varieties developed from the use of XB33H12, as well as cells and other plant parts thereof. Plants of the invention include any plant having at least 90%, 91%, 92%, 93%, 94%, 95%, 96%, 97%, 98%, 99%, 99.5%, or 99.9% of the markers in the SSR profile, and that retain 90%, 91%, 92%, 93%, 94%, 95%, 96%, 97%, 98%, 99%, 99.5%, or 99.9% of the physiological and morphological characteristics of variety XB33H12 when grown under the same conditions. Such plants may be developed using the markers identified in WO 00/31964, U.S. Pat. No. 6,162,967 and U.S. Pat. No. 7,288,386. Progeny plants and plant parts produced using XB33H12 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from soybean variety XB33H12, as measured by either percent identity or percent similarity. Such progeny may be further characterized as being within a pedigree distance of XB33H12, such as within 1, 2, 3, 4, or 5 or less cross-pollinations to a soybean plant other than XB33H12, or a plant that has XB33H12 as a progenitor. Unique molecular profiles may be identified with other molecular tools such as SNPs and RFLPs.

Introduction of a New Trait or Locus into XB33H12

Variety XB33H12 represents a new base genetic variety into which a new locus or trait may be introgressed. Direct transformation and backcrossing represent two important methods that can be used to accomplish such an introgression.

A backcross conversion of XB33H12 occurs when DNA sequences are introduced through backcrossing (Hallauer et al. in Corn and Corn Improvement, Sprague and Dudley, Third Ed. 1998) with XB33H12 utilized as the recurrent parent. Both naturally occurring and transgenic DNA sequences may be introduced through backcrossing techniques. A backcross conversion may produce a plant with a trait or locus conversion in at least two or more backcrosses, including at least 2 backcrosses, at least 3 backcrosses, at least 4 backcrosses, at least 5 backcrosses, or more. Molecular marker assisted breeding or selection may be utilized to reduce the number of backcrosses necessary to achieve the backcross conversion. For example, see Openshaw et al., "Marker-assisted Selection in Backcross Breeding". In: Proceedings Symposium of the Analysis of Molecular Data, August 1994, Crop Science Society of America, Corvallis, Oreg., which demonstrated that a backcross conversion can be made in as few as two backcrosses.

The complexity of the backcross conversion method depends on the type of trait being transferred (a single gene or closely linked genes compared to unlinked genes), the level of expression of the trait, the type of inheritance (cytoplasmic or nuclear), dominant or recessive trait expression, and the types of parents included in the cross. It is understood by those of ordinary skill in the art that for single gene traits that are relatively easy to classify, the backcross method is effective and relatively easy to manage. (See Hallauer et al., in Corn and Corn Improvement, Sprague and Dudley, Third Ed. 1998). Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal, or viral), insect resistance, and herbicide resistance. In addition, a recombination site itself, such as an FRT site, Lox site, or other site specific integration site, may be inserted by backcrossing and utilized for direct insertion of one or more genes of interest into a specific plant variety. A single locus may contain several transgenes, such as a transgene for disease resistance and a transgene for herbicide resistance. The gene for herbicide resistance may be used as a selectable marker and/or as a phenotypic trait. A single locus conversion of site specific integration system allows for the integration of multiple genes at a known recombination site in the genome.

The backcross conversion may result from either the transfer of a dominant allele or a recessive allele. Selection of progeny containing the trait of interest can be accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the trait(s) being transferred, although a backcross conversion with a stably introgressed trait may also be maintained by further backcrossing to the recurrent parent with subsequent selection for the trait.

Along with selection for the trait of interest, progeny are selected for the phenotype of the recurrent parent. The backcross is a form of inbreeding, and the features of the recurrent parent are automatically recovered after successive backcrosses. Poehlman suggests from one to four or more backcrosses, but as noted above, the number of backcrosses necessary can be reduced with the use of molecular markers (Poehlman et al., (1995) Breeding Field Crops, 4th Ed., Iowa State University Press, Ames, Iowa). Other factors, such as a genetically similar donor parent, may also reduce the number of backcrosses necessary. As noted by Poehlman, backcrossing is easiest for simply inherited, dominant, and easily recognized traits.

One process for adding or modifying a trait or locus in soybean variety XB33H12 comprises crossing XB33H12 plants grown from XB33H12 seed with plants of another soybean plant that comprises a desired trait lacking in XB33H12, selecting F1 progeny plants that possess the desired trait or locus to produce selected F1 progeny plants, crossing the selected progeny plants back to XB33H12 plants to produce backcross) (BC1) progeny plants. The BC1F1 progeny plants that have the desired trait and the morphological characteristics of soybean variety XB33H12 are selected and backcrossed to XB33H12 to generate BC2F1 progeny plants. Additional backcrossing and selection of progeny plants with the desired trait will produce BC3F1, BC4F1, BC5F1, . . . BCxF1 generations of plants. The backcross populations of XB33H12 may be further characterized as having the physiological and morphological characteristics of soybean variety XB33H12 listed in Table 1 as determined at the 5% significance level when grown in the same environmental conditions and/or may be characterized by percent similarity or identity to XB33H12 as determined by SSR or other molecular markers. The above method may be utilized with fewer backcrosses in appropriate situations, such as when the donor parent is highly related or molecular markers are used in one or more selection steps. Desired traits that may be used include those nucleic acids known in the art, some of which are listed herein, that will affect traits through nucleic acid expression or inhibition. Desired loci also include the introgression of FRT, Lox, and/or other recombination sites for site specific integration. Desired loci further include QTLs, which may also affect a desired trait.

In addition, the above process and other similar processes described herein may be used to produce first generation progeny soybean seed by adding a step at the end of the process that comprises crossing XB33H12 with the introgressed trait or locus with a different soybean plant and harvesting the resultant first generation progeny soybean seed.

Transgenes and transformation methods provide means to engineer the genome of plants to contain and express heterologous genetic elements, including but not limited to foreign genetic elements, additional copies of endogenous elements, and/or modified versions of native or endogenous genetic elements, in order to alter at least one trait of a plant in a specific manner that would be difficult or impossible to obtain with traditional plant breeding alone. Any heterologous DNA sequence(s), whether from a different species or from the same species, which are inserted into the genome using transformation, backcrossing, or other methods known to one of skill in the art are referred to herein collectively as transgenes. The sequences are heterologous based on sequence source, location of integration, operably linked elements, or any combination thereof. One or more transgenes of interest can be introduced into soybean variety XB33H12. Transgenic variants of soybean variety XB33H12 plants, seeds, cells, and parts thereof or derived therefrom are provided. Transgenic variants of XB33H12 comprise the physiological and morphological characteristics of soybean variety XB33H12 listed in Table 1 as determined at the 5% significance level when grown in the same environmental conditions, and/or may be characterized or identified by percent similarity or identity to XB33H12 as determined by SSR or other molecular markers. In some examples, transgenic variants of soybean variety XB33H12 are produced by introducing at least one transgene of interest into soybean variety XB33H12 by transforming XB33H12 with a polynucleotide comprising the transgene of interest. In other examples, transgenic variants of soybean variety XB33H12 are produced by introducing at least one transgene by introgressing the transgene into soybean variety XB33H12 by crossing.

In one example, a process for modifying soybean variety XB33H12 with the addition of a desired trait, said process comprising transforming a soybean plant of variety XB33H12 with a transgene that confers a desired trait is provided. Therefore, transgenic XB33H12 soybean cells, plants, plant parts, and seeds produced from this process are provided. In some examples one more desired traits may include traits such as herbicide resistance, insect resistance, disease resistance, decreased phytate, modified fatty acid profile, modified fatty acid content, carbohydrate metabolism, protein content, or oil content. The specific gene may be any known in the art or listed herein, including but not limited to a polynucleotide conferring resistance to imidazolinone, sulfonylurea, protoporphyrinogen oxidase (PPO) inhibitors, hydroxyphenyl pyruvate dioxygenase (HPPD) inhibitors, glyphosate, glufosinate, triazine, 2,4-dichlorophenoxyacetic acid (2,4-D), dicamba, broxynil, metribuzin, or benzonitrile herbicides; a polynucleotide encoding a *Bacillus thuringiensis* polypeptide, a polynucleotide encoding a phytase, a fatty acid desaturase (e.g., FAD-2, FAD-3), galactinol synthase, a raffinose synthetic enzyme; or a polynucleotide conferring resistance to soybean cyst nematode, brown stem rot, *Phy-* tophthora root rot, soybean mosaic virus, sudden death syndrome, or other plant pathogen.

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88; and Armstrong (1999) "The First Decade of Maize Transformation: A Review and Future Perspective" Maydica 44:101-109. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

The most prevalent types of plant transformation methods involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into the genome of a particular soybean plant may then be moved into the genome of another variety using traditional breeding techniques that are well known in the plant breeding arts. For example, a backcrossing approach is commonly used to move a transgene from a transformed soybean variety into an elite soybean variety, and the resulting backcross conversion plant would then contain the transgene(s).

Various genetic elements can be introduced into the plant genome using transformation. These elements include, but are not limited to genes; coding sequences; inducible, constitutive, and tissue specific promoters; enhancing sequences; and signal and targeting sequences.

Transgenic plants can be used to produce commercial quantities of a foreign protein. Thus, techniques for the selection and propagation of transformed plants, which are well understood in the art, yield a plurality of transgenic plants that are harvested in a conventional manner, and a heterologous protein then can be extracted from a tissue of interest or from total biomass. Protein extraction from plant biomass can be accomplished by known methods which are discussed, for example, by Heney and Orr (1981) Anal. Biochem. 114:92-6.

A genetic map can be generated that identifies the approximate chromosomal location of the integrated DNA molecule, for example via conventional restriction fragment length polymorphisms (RFLP), polymerase chain reaction (PCR) analysis, simple sequence repeats (SSR), and single nucleotide polymorphisms (SNP). For exemplary methodologies in this regard, see Glick and Thompson, Methods in Plant Molecular Biology and Biotechnology, pp. 269-284 (CRC Press, Boca Raton, 1993).

Wang et al. discuss "Large Scale Identification, Mapping and Genotyping of Single-Nucleotide Polymorphisms in the Human Genome", Science (1998) 280:1077-1082, and similar capabilities are increasingly available for the soybean genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons could involve hybridizations, RFLP, PCR, SSR, sequencing or combinations thereof, all of which are conventional techniques. SNPs may also be used alone or in combination with other techniques.

Likewise, plants can be genetically engineered to express various phenotypes of agronomic interest. Through the transformation of soybean the expression of genes can be altered to enhance disease resistance, insect resistance, herbicide resistance, agronomic, grain quality, and other traits. Transformation can also be used to insert DNA sequences which control or help control male-sterility. DNA sequences native to soybean as well as non-native DNA sequences can be transformed into soybean and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing or gene suppression) is desirable for several aspects of genetic engineering in plants.

Many techniques for gene silencing are well known to one of skill in the art, including but not limited to, knock-outs (such as by insertion of a transposable element such as mu (Vicki Chandler, The Maize Handbook ch. 118 (Springer-Verlag 1994); antisense technology (see, e.g., Sheehy et al. (1988) PNAS USA 85:8805-8809; and U.S. Pat. Nos. 5,107,065; 5,453,566; and 5,759,829); co-suppression (e.g., Taylor (1997) Plant Cell 9:1245; Jorgensen (1990) Trends Biotech. 8:340-344; Flavell (1994) PNAS USA 91:3490-3496; Finnegan et al. (1994) Bio/Technology 12:883-888; and Neuhuber et al. (1994) Mol. Gen. Genet. 244:230-241); RNA interference (Napoli et al. (1990) Plant Cell 2:279-289; U.S. Pat. No. 5,034,323; Sharp (1999) Genes Dev. 13:139-141; Zamore et al. (2000) Cell 101:25-33; and Montgomery et al. (1998) PNAS USA 95:15502-15507); virus-induced gene silencing (Burton et al. (2000) Plant Cell 12:691-705; and Baulcombe (1999) Curr. Op. Plant Biol. 2:109-113); target-RNA-specific ribozymes (Haseloff et al. (1988) Nature 334: 585-591); hairpin structures (Smith et al. (2000) Nature 407:319-320; WO 99/53050; and WO 98/53083); microRNA (Aukerman & Sakai (2003) Plant Cell 15:2730-2741); ribozymes (Steinecke et al. (1992) EMBO J. 11:1525; and Perriman et al. (1993) Antisense Res. Dev. 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Exemplary nucleotide sequences that may be altered by genetic engineering include, but are not limited to, those categorized below.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al. (1994) Science 266: 789 (cloning of the tomato Cf-9 gene for resistance to *Cladosporium fulvum*); Martin et al. (1993) Science 262:1432 (tomato Pto gene for resistance to *Pseudomonas syringae* pv. tomato encodes a protein kinase); Mindrinos et al. (1994) Cell 78:1089 (*Arabidopsis* RPS2 gene for resistance to *Pseudomonas syringae*), McDowell & Woffenden (2003) Trends Biotechnol. 21:178-83; and Toyoda et al. (2002) Transgenic Res. 11:567-82. A plant resistant to a disease is one that is more resistant to a pathogen as compared to the wild type plant.

(B) A *Bacillus thuringiensis* (Bt) protein, a derivative thereof or a synthetic polypeptide modeled thereon. See, for example, Geiser et al. (1986) Gene 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995, and 31998. Other non-limiting examples of *Bacillus thuringiensis* transgenes being genetically engineered are given in the following patents and patent applications, and hereby are incorporated by reference for this purpose: U.S. Pat. Nos. 5,188,960; 5,689,052; 5,880,275; 5,986,177; 7,105,332; 7,208,474; WO 91/14778; WO 99/31248; WO 01/12731; WO 99/24581; WO 97/40162; US2002/0151709; US2003/0177528; US2005/0138685; US/20070245427; US2007/0245428; US2006/0241042; US2008/0020966; US2008/0020968; US2008/0020967; US2008/0172762; US2008/0172762; and US2009/0005306.

(C) An insect-specific hormone or pheromone such as an ecdysteroid or juvenile hormone, a variant thereof, a mimetic based thereon, or an antagonist or agonist thereof. See, for example, the disclosure by Hammock et al. (1990) Nature 344:458, of baculovirus expression of cloned juvenile hormone esterase, an inactivator of juvenile hormone.

(D) An insect-specific peptide which, upon expression, disrupts the physiology of the affected pest. For example, see the disclosures of Regan (1994) J. Biol. Chem. 269:9 (expression cloning yields DNA coding for insect diuretic hormone receptor); Pratt et al. (1989) Biochem. Biophys. Res. Comm. 163:1243 (an allostatin is identified in *Diploptera puntata*); Chattopadhyay et al. (2004) Critical Reviews in Microbiology 30:33-54 2004; Zjawiony (2004) J Nat Prod 67:300-310; Carlini & Grossi-de-Sa (2002) Toxicon 40:1515-1539; Ussuf et al. (2001) Curr Sci. 80:847-853; and Vasconcelos & Oliveira (2004) Toxicon 44:385-403. See also U.S. Pat. No. 5,266,317 to Tomalski et al., who disclose genes encoding insect-specific toxins.

(E) An enzyme responsible for a hyperaccumulation of a monoterpene, a sesquiterpene, a steroid, hydroxamic acid, a phenylpropanoid derivative, or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See WO 93/02197, which discloses the nucleotide sequence of a callase gene. DNA molecules which contain chitinase-encoding sequences can be obtained, for example, from the ATCC under Accession Nos. 39637 and 67152. See also Kramer et al. (1993) Insect Biochem. Molec. Biol. 23:691, who teach the nucleotide sequence of a cDNA encoding tobacco hookworm chitinase, and Kawalleck et al. (1993) Plant Mol. Biol. 21:673, who provide the nucleotide sequence of the parsley ubi4-2 polyubiquitin gene, and U.S. Pat. Nos. 6,563,020; 7,145,060; and 7,087,810.

(G) A molecule that stimulates signal transduction. For example, see the disclosure by Botella et al. (1994) Plant Mol. Biol. 24:757, of nucleotide sequences for mung bean calmodulin cDNA clones, and Griess et al. (1994) Plant Physiol. 104:1467, which provides the nucleotide sequence of a maize calmodulin cDNA clone.

(H) A hydrophobic moment peptide. See WO 95/16776 and U.S. Pat. No. 5,580,852 disclosure of peptide derivatives of tachyplesin which inhibit fungal plant pathogens, and WO 95/18855 and U.S. Pat. No. 5,607,914 which teach synthetic antimicrobial peptides that confer disease resistance.

(I) A membrane permease, a channel former, or a channel blocker. For example, see the disclosure by Jaynes et al. (1993) Plant Sci. 89:43, of heterologous expression of a cecropin-beta lytic peptide analog to render transgenic tobacco plants resistant to *Pseudomonas solanacearum*.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al. (1990) Ann. Rev. Phytopathol. 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus.

(K) An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Intl Symposium on Molecular Plant-Microbe Interactions (Edinburgh, Scotland, 1994) (enzymatic inactivation in transgenic tobacco via production of single-chain antibody fragments).

(L) A virus-specific antibody. See, for example, Tavladoraki et al. (1993) Nature 366:469, who show that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al. (1992) Bio/Technology 10:1436. The cloning and characterization of a gene which encodes a bean endopolygalacturonase-inhibiting protein is described by Toubart et al. (1992) Plant J. 2:367.

(N) A developmental-arrestive protein produced in nature by a plant. For example, Logemann et al. (1992) Bio/Technology 10:305, have shown that transgenic plants expressing the barley ribosome-inactivating gene have an increased resistance to fungal disease.

(O) Genes involved in the systemic acquired resistance (SAR) Response and/or the pathogenesis related genes. Briggs (1995) Current Biology 5:128-131, Pieterse & Van Loon (2004) Curr. Opin. Plant Bio. 7:456-64; and Somssich (2003) Cell 113:815-6.

(P) Antifungal genes (Cornelissen and Melchers (1993) Plant Physiol. 101:709-712; Parijs et al. (1991) Planta 183:258-264; Bushnell et al. (1998) Can. J. Plant Path. 20:137-149. Also, see US2002/0166141; US2007/0274972; US2007/0192899; US2008/0022426; and U.S. Pat. Nos. 6,891,085; 7,306,946; and 7,598,346.

(Q) Detoxification genes, such as for fumonisin, beauvericin, moniliformin, zearalenone, and their structurally related derivatives. For example, see U.S. Pat. Nos. 5,716,820; 5,792, 931; 5,798,255; 5,846,812; 6,083,736; 6,538,177; 6,388,171; and 6,812,380.

(R) Cystatin and cysteine proteinase inhibitors. See U.S. Pat. No. 7,205,453.

(S) Defensin genes. See WO 03/000863 and U.S. Pat. Nos. 6,911,577; 6,855,865; 6,777,592; and 7,238,781.

(T) Genes conferring resistance to nematodes. See e.g. WO 96/30517; WO 93/19181; WO 03/033651; and Urwin et al.

(1998) Planta 204:472-479; Williamson (1999) Curr Opin Plant Bio. 2:327-31; and U.S. Pat. Nos. 6,284,948 and 7,301,069.

(U) Genes that confer resistance to *Phytophthora* Root Rot, such as Rps1, Rps1-a, Rps1-b, Rps1-c, Rps1-d, Rps1-e, Rps1-k, Rps2, Rps3-a, Rps3-b, Rps3-c, Rps4, Rps5, Rps6, Rps7, Rps8, and other Rps genes. See, for example, Shoemaker et al. "*Phytophthora* Root Rot Resistance Gene Mapping in Soybean", Plant Genome IV Conference, San Diego, Calif. (1995).

(V) Genes that confer resistance to Brown Stem Rot, such as described in U.S. Pat. No. 5,689,035, and incorporated by reference for this purpose.

2. Transgenes that Confer Resistance to a Herbicide, for Example:

(A) A herbicide that inhibits the growing point or meristem, such as an imidazolinone, or a sulfonylurea. Exemplary genes include mutant ALS and AHAS enzymes as described, for example, by Lee et al. (1988) EMBO J. 7:1241; and, Miki et al. (1990) Theor. Appl. Genet. 80:449, respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; US2007/0214515; and WO 96/33270.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,566,587; 6,338,961; 6,248,876; 6,040,497; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; RE 36,449; RE 37,287; and 5,491,288; and EP1173580; WO 01/66704; EP1173581; and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition, glyphosate resistance can be imparted to plants by the overexpression of genes encoding glyphosate N-acetyltransferase. See, for example, US2004/0082770; US2005/0246798; and US2008/0234130 which are incorporated herein by reference for this purpose. A DNA molecule encoding a mutant aroA gene can be obtained under ATCC accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European Patent No. 0 242 246 and 0 242 236 to Leemans et al. De Greef et al. (1989) Bio/Technology 7:61 describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616; and 5,879,903, which are incorporated herein by reference for this purpose. Exemplary genes conferring resistance to phenoxy proprionic acids and cyclohexones, such as sethoxydim and haloxyfop, are the Acc1-S1, Acc1-S2, and Acc1-S3 genes described by Marshall et al. (1992) Theor. Appl. Genet. 83:435.

(C) A herbicide that inhibits photosynthesis, such as a triazine (psbA and gs+ genes) and a benzonitrile (nitrilase gene). Przibilla et al. (1991) Plant Cell 3:169, describe the transformation of *Chlamydomonas* with plasmids encoding mutant psbA genes. Nucleotide sequences for nitrilase genes are disclosed in U.S. Pat. No. 4,810,648, and DNA molecules containing these genes are available under ATCC Accession Nos. 53435, 67441, and 67442. Cloning and expression of DNA coding for a glutathione S-transferase is described by Hayes et al. (1992) Biochem. J. 285:173.

(D) Acetohydroxy acid synthase, which has been found to make plants that express this enzyme resistant to multiple types of herbicides, has been introduced into a variety of plants (see, e.g., Hattori et al. (1995) Mol Gen Genet 246: 419). Other genes that confer resistance to herbicides include: a gene encoding a chimeric protein of rat cytochrome P4507A1 and yeast NADPH-cytochrome P450 oxidoreductase (Shiota et al. (1994) Plant Physiol 106:17), genes for glutathione reductase and superoxide dismutase (Aono et al. (1995) Plant Cell Physiol 36:1687), and genes for various phosphotransferases (Datta et al. (1992) Plant Mol Biol 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; and 5,767,373; and WO 01/12825.

3. Transgenes that Confer or Contribute to a Grain and/or Seed Characteristic, Such as:

(A) Fatty acid profile(s), for example, by
(1) Down-regulation of stearoyl-ACP desaturase to increase stearic acid content of the plant. See Knultzon et al. (1992) Proc. Natl. Acad. Sci. USA 89:2624; and WO 99/64579 (Genes for Desaturases to Alter Lipid Profiles in Corn).
(2) Elevating oleic acid via FAD-2 gene modification and/or decreasing linolenic acid via FAD-3 gene modification (see U.S. Pat. Nos. 6,063,947; 6,323,392; 6,372,965; and WO 93/11245).
(3) Altering conjugated linolenic or linoleic acid content, such as in WO 01/12800.
(4) Altering LEC1, AGP, mi1ps, and various Ipa genes such as Ipa1, Ipa3, hpt or hggt. For example, see WO 02/42424; WO 98/22604; WO 03/011015; U.S. Pat. Nos. 6,423,886; 6,197,561; and, 6,825,397; US2003/0079247; US2003/0204870; WO 02/057439; WO 03/011015; and Rivera-Madrid et al. (1995) Proc. Natl. Acad. Sci. 92:5620-5624.

B) Altered phosphorus content, for example, by:
(1) Introduction of a phytase-encoding gene would enhance breakdown of phytate, adding more free phosphate to the transformed plant. For example, see Van Hartingsveldt et al. (1993) Gene 127:87, for a disclosure of the nucleotide sequence of an *Aspergillus niger* phytase gene.
(2) Modulating a gene that reduces phytate content. For example in maize this could be accomplished by cloning and then re-introducing DNA associated with one or more of the alleles, such as the LPA alleles, identified in maize mutants characterized by low levels of phytic acid, such as in WO 05/113778; and/or by altering inositol kinase activity as in WO 02/059324; U.S. Pat. No. 7,067,720; WO 03/027243; US2003/0079247; WO 99/05298; U.S. Pat. Nos. 6,197,561; 6,291,224; and 6,391,348; WO 98/45448; WO 99/55882; and WO 01/04147.

(C) Altered carbohydrates, for example, by altering a gene for an enzyme that affects the branching pattern of starch or, a gene altering thioredoxin such as NTR and/or TRX (see U.S. Pat. No. 6,531,648 which is incorporated by reference for this purpose). See Shiroza et al. (1988) J. Bacteriol. 170: 810 (nucleotide sequence of *Streptococcus mutans* fructosyltransferase gene); Steinmetz et al. (1985) Mol. Gen. Genet. 200:220 (nucleotide sequence of *Bacillus subtilis* levansucrase gene); Pen et al. (1992) Bio/Technology 10:292 (production of transgenic plants that express *Bacillus licheniformis* alpha-amylase); Elliot et al. (1993) Plant Mol. Biol. 21:515 (nucleotide sequences of tomato invertase genes); Søgaard et al. (1993) J. Biol. Chem. 268:22480 (site-directed mutagenesis of barley alpha-amylase gene); Fisher et al. (1993) Plant Physiol. 102:1045 (maize endosperm starch branching enzyme II); WO 99/10498 (improved digestibility and/or starch extraction through modification of UDP-D-xylose 4-epimerase, Fragile 1 and 2, Ref1, HCHL, C4H); and, U.S. Pat. No. 6,232,529 (method of producing high oil seed by modification of starch levels (AGP). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see U.S. Pat. Nos. 6,787,683; 7,154,029; and WO 00/68393 involving the manipulation of antioxidant levels, and WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds); U.S. Pat. No. 6,080,913 (binary methods of increasing accumulation of essential amino acids in seeds); U.S. Pat. No. 5,990,389 (high lysine); WO 99/40209 (alteration of amino acid compositions in seeds); WO 99/29882 (methods for altering amino acid content of proteins); U.S. Pat. No. 5,850,016 (alteration of amino acid compositions in seeds); WO 98/20133 (proteins with enhanced levels of essential amino acids); U.S. Pat. No. 5,885,802 (high methionine); U.S. Pat. No. 5,885,801 (high threonine); U.S. Pat. No. 6,664,445 (plant amino acid biosynthetic enzymes); U.S. Pat. No. 6,459,019 (increased lysine and threonine); U.S. Pat. No. 6,441,274 (plant tryptophan synthase beta subunit); U.S. Pat. No. 6,346,403 (methionine metabolic enzymes); U.S. Pat. No. 5,939,599 (high sulfur); U.S. Pat. No. 5,912,414 (increased methionine); WO 98/56935 (plant amino acid biosynthetic enzymes); WO 98/45458 (engineered seed protein having higher percentage of essential amino acids); WO 98/42831 (increased lysine); U.S. Pat. No. 5,633,436 (increasing sulfur amino acid content); U.S. Pat. No. 5,559,223 (synthetic storage proteins with defined structure containing programmable levels of essential amino acids); WO 96/01905 (increased threonine); WO 95/15392 (increased lysine); U.S. Pat. Nos. 6,930,225; 7,179,955; 6,803,498; US2004/0068767; and WO 01/79516.

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar et al., and chromosomal translocations as described by Patterson in U.S. Pat. Nos. 3,861,709 and 3,710,511. In addition to these methods, Albertsen et al. U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed. Male sterile soybean lines and characterization are discussed in Palmer (2000) Crop Sci 40:78-83, and Jin et al. (1997) Sex Plant Reprod 10:13-21.

(A) Introduction of a deacetylase gene under the control of a tapetum-specific promoter and with the application of the chemical N-Ac-PPT (WO 01/29237).

(B) Introduction of various stamen-specific promoters (WO 92/13956 and WO 92/13957).

(C) Introduction of the barnase and the barstar gene (Paul et al. (1992) Plant Mol. Biol. 19:611-622).

For additional examples of nuclear male and female sterility systems and genes, see also, U.S. Pat. Nos. 5,859,341; 6,297,426; 5,478,369; 5,824,524; 5,850,014; and 6,265,640; all of which are hereby incorporated by reference.

5. Polynucleotides comprising a sequence for site specific DNA recombination. This includes the introduction of at least one FRT site that may be used in the FLP/FRT system and/or a Lox site that may be used in the Cre/Lox system. For example, see Lyznik et al. (2003) Plant Cell Rep 21:925-932; and WO 99/25821, which are hereby incorporated by reference. Other systems that may be used include the Gin recombinase of phage Mu (Maeser et al. (1991) Mol Gen Genet. 230:170-176); the Pin recombinase of *E. coli* (Enomoto et al. (1983) J Bacteriol 156:663-668); and the R/RS system of the pSR1 plasmid (Araki et al. (1992) J Mol Biol 182:191-203).

6. Genes that affect abiotic stress resistance (including but not limited to flowering, flower development, pod, and seed development, enhancement of nitrogen utilization efficiency, altered nitrogen responsiveness, drought resistance or tolerance, cold resistance or tolerance, and salt resistance or tolerance) and increased yield under stress. For example, see WO 00/73475 where water use efficiency is altered through alteration of malate; U.S. Pat. Nos. 5,892,009; 5,965,705; 5,929,305; 5,891,859; 6,417,428; 6,664,446; 6,706,866; 6,717,034; and 6,801,104; WO 00/060089; WO 01/026459; WO 00/1035725; WO 01/034726; WO 01/035727; WO 00/1036444; WO 01/036597; WO 01/036598; WO 00/2015675; WO 02/017430; WO 02/077185; WO 02/079403; WO 03/013227; WO 03/013228; WO 03/014327; WO 04/031349; WO 04/076638; WO 98/09521; and WO 99/38977 describing genes, including CBF genes (C-repeat/DRE-Binding Factor, see, e.g., Stockinger et al. 1997 PNAS 94:1035-1040) and transcription factors effective in mitigating the negative effects of freezing, high salinity, and drought on plants, as well as conferring other positive effects on plant phenotype; US2004/0148654 and WO 01/36596 where abscisic acid is altered in plants resulting in improved plant phenotype such as increased yield and/or increased tolerance to abiotic stress; WO 00/006341, WO 04/090143, U.S. Pat. Nos. 7,531,723, and 6,992,237 where cytokinin expression is modified resulting in plants with increased stress tolerance, such as drought tolerance, and/or increased yield. Also see WO 02/02776, WO 03/052063, JP2002281975, U.S. Pat. No. 6,084,153, WO 01/64898, U.S. Pat. No. 6,177,275, and U.S.

Pat. No. 6,107,547 (enhancement of nitrogen utilization and altered nitrogen responsiveness). For ethylene alteration, see US2004/0128719, US2003/0166197, and WO 00/32761. For plant transcription factors or transcriptional regulators of abiotic stress, see e.g. US2004/0098764 or US2004/0078852.

Other genes and transcription factors that affect plant growth and agronomic traits such as yield, flowering, plant growth, and/or plant structure, can be introduced or introgressed into plants, see e.g., WO 97/49811 (LHY), WO 98/56918 (ESD4), WO 97/10339, and U.S. Pat. No. 6,573, 430 (TFL), U.S. Pat. No. 6,713,663 (FT), WO 96/14414 (CON), WO 96/38560, WO 01/21822 (VRN1), WO 00/44918 (VRN2), WO 99/49064 (GI), WO 00/46358 (FRI), WO 97/29123, U.S. Pat. No. 6,794,560, U.S. Pat. No. 6,307, 126 (GAI), WO 99/09174 (D8 and Rht), and WO 04/076638 and WO 04/031349 (transcription factors).

Development of Soybean Sublines

Sublines of XB33H12 may also be developed and are provided. Although XB33H12 contains substantially fixed genetics and is phenotypically uniform with no off-types expected, there still remains a small proportion of segregating loci either within individuals or within the population as a whole. Sublining provides the ability to select for these loci, which have no apparent morphological or phenotypic effect on the plant characteristics, but may have an effect on overall yield. For example, the methods described in U.S. Pat. Nos. 5,437,697, 7,973,212, and US2011/0258733, and US2011/ 0283425 (each of which is herein incorporated by reference) may be utilized by a breeder of ordinary skill in the art to identify genetic loci that are associated with yield potential to further purify the variety in order to increase its yield. A breeder of ordinary skill in the art may fix agronomically important loci by making them homozygous in order to optimize the performance of the variety. The development of soybean sublines and the use of accelerated yield technology is a plant breeding technique.

Soybean varieties such as XB33H12 are typically developed for use in seed and grain production. However, soybean varieties such as XB33H12 also provide a source of breeding material that may be used to develop new soybean varieties. Plant breeding techniques known in the art and used in a soybean plant breeding program include, but are not limited to, recurrent selection, mass selection, bulk selection, backcrossing, pedigree breeding, open pollination breeding, restriction fragment length polymorphism enhanced selection, genetic marker enhanced selection, making double haploids, and transformation. Often combinations of these techniques are used. The development of soybean varieties in a plant breeding program requires, in general, the development and evaluation of homozygous varieties. There are many analytical methods available to evaluate a new variety. The oldest and most traditional method of analysis is the observation of phenotypic traits but genotypic analysis may also be used.

Methods for producing a soybean plant by crossing a first parent soybean plant with a second parent soybean plant wherein the first and/or second parent soybean plant is variety XB33H12 are provided. Also provided are methods for producing a soybean plant having substantially all of the morphological and physiological characteristics of variety XB33H12, by crossing a first parent soybean plant with a second parent soybean plant wherein the first and/or the second parent soybean plant is a plant having substantially all of the morphological and physiological characteristics of variety XB33H12 set forth in Table 1, as determined at the 5% significance level when grown in the same environmental conditions. The other parent may be any soybean plant, such as a soybean plant that is part of a synthetic or natural population. Any such methods using soybean variety XB33H12 include but are not limited to selfing, sibbing, backcrossing, mass selection, pedigree breeding, bulk selection, hybrid production, crossing to populations, and the like. These methods are well known in the art and some of the more commonly used breeding methods are described below. Descriptions of breeding methods can be found in one of several reference books (e.g., Allard, *Principles of Plant Breeding*, 1960; Simmonds, *Principles of Crop Improvement*, 1979; Fehr, "Breeding Methods for Cultivar Development", Chapter 7, *Soybean Improvement, Production and Uses*, $2^{nd}$ ed., Wilcox editor, 1987).

Pedigree breeding starts with the crossing of two genotypes, such as XB33H12 or a soybean variety having all of the morphological and physiological characteristics of XB33H12, and another soybean variety having one or more desirable characteristics that is lacking or which complements XB33H12. If the two original parents do not provide all the desired characteristics, other sources can be included in the breeding population. In the pedigree method, superior plants are selfed and selected in successive filial generations. In the succeeding filial generations, the heterozygous allele condition gives way to the homozygous allele condition as a result of inbreeding. Typically in the pedigree method of breeding, five or more successive filial generations of selfing and selection are practiced: e.g., F1→F2; F2→F3; F3→F4; F4→F5; etc. In some examples, 1, 2, 3, 4, 5, 6, 7, 8, 9, 10, or more generations of selfing and selection are practiced. After a sufficient amount of inbreeding, successive filial generations will serve to increase seed of the developed variety. Typically, the developed variety comprises homozygous alleles at about 95% or more of its loci.

In addition to being used to create backcross conversion populations, backcrossing can also be used in combination with pedigree breeding. As discussed previously, backcrossing can be used to transfer one or more specifically desirable traits from one variety (the donor parent) to a developed variety (the recurrent parent), which has good overall agronomic characteristics yet may lack one or more other desirable traits. However, the same procedure can be used to move the progeny toward the genotype of the recurrent parent but at the same time retain many components of the non-recurrent parent by stopping the backcrossing at an early stage and proceeding with selfing and selection. For example, a soybean variety may be crossed with another variety to produce a first generation progeny plant. The first generation progeny plant may then be backcrossed to one of its parent varieties to create a BC1F1. Progeny are selfed and selected so that the newly developed variety has many of the attributes of the recurrent parent and yet several of the desired attributes of the donor parent. This approach leverages the value and strengths of both parents for use in new soybean varieties.

Therefore, in some examples a method of making a backcross conversion of soybean variety XB33H12, comprising the steps of crossing a plant of soybean variety XB33H12 or a soybean variety having all of the morphological and physiological characteristics of XB33H12 with a donor plant possessing a desired trait to introduce the desired trait, selecting an F1 progeny plant containing the desired trait, and backcrossing the selected F1 progeny plant to a plant of soybean variety XB33H12 are provided. This method may further comprise the step of obtaining a molecular marker profile of soybean variety XB33H12 and using the molecular marker profile to select for a progeny plant with the desired trait and the molecular marker profile of XB33H12. The molecular marker profile can comprise information from one or more markers. In one example the desired trait is a mutant gene or transgene present in the donor parent. In another example, the desired trait is a native trait in the donor parent.

Recurrent selection is a method used in a plant breeding program to improve a population of plants. Variety XB33H12, and/or a soybean variety having all of the morphological and physiological characteristics of XB33H12, is suitable for use in a recurrent selection program. The method entails individual plants cross pollinating with each other to form progeny. The progeny are grown and the superior progeny selected by any number of selection methods, which include individual plant, half-sib progeny, full-sib progeny, and selfed progeny. The selected progeny are cross pollinated with each other to form progeny for another population. This population is planted and, again, superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self pollination, directed pollination could be used as part of the breeding program.

Mutation breeding is another method of introducing new traits into soybean variety XB33H12 or a soybean variety having all of the morphological and physiological characteristics of XB33H12. Mutations that occur spontaneously or that are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, gamma rays (e.g., cobalt 60 or cesium 137), neutrons, (product of nuclear fission by uranium 235 in an atomic reactor), beta radiation (emitted from radioisotopes such as phosphorus 32 or carbon 14), ultraviolet radiation (preferably from 2500 to 2900 nm), or chemical mutagens such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis, the trait may then be incorporated into existing germplasm by traditional breeding techniques. Details of mutation breeding can be found in "Principles of Cultivar Development" Fehr, 1993, Macmillan Publishing Company. In addition, mutations created in other soybean plants may be used to produce a backcross conversion of XB33H12 that comprises such mutation.

Molecular markers, which include markers identified through the use of techniques such as isozyme electrophoresis, restriction fragment length polymorphisms (RFLPs), randomly amplified polymorphic DNAs (RAPDs), arbitrarily primed polymerase chain reaction (AP-PCR), DNA amplification fingerprinting (DAF), sequence characterized amplified regions (SCARs), amplified fragment length polymorphisms (AFLPs), simple sequence repeats (SSRs), and single nucleotide polymorphisms (SNPs), may be used in plant breeding methods utilizing XB33H12.

Isozyme electrophoresis and RFLPs have been widely used to determine genetic composition. Shoemaker and Olsen ("Molecular Linkage Map of Soybean (*Glycine max* L. Merr.)", p. 6.131-6.138. In S. J. O'Brien (ed.) Genetic Maps: Locus Maps of Complex Genomes. (1993) Cold Spring Harbor Laboratory Press. Cold Spring Harbor, N.Y.), developed a molecular genetic linkage map that consisted of 25 linkage groups with about 365 RFLP, 11 RAPD (random amplified polymorphic DNA), three classical markers, and four isozyme loci. See also, Shoemaker "RFLP Map of Soybean". pp 299-309 (1994). In R. L. Phillips and I. K. Vasil (ed.) DNA-based markers in plants. Kluwer Academic Press Dordrecht, the Netherlands.

SSR technology is an efficient and practical marker technology; more marker loci can be routinely used and more alleles per marker locus can be found using SSRs in comparison to RFLPs. For example, Diwan and Cregan, described highly polymorphic microsatellite loci in soybean with as many as 26 alleles. (Diwan and Cregan (1997) Theor. Appl. Genet. 95:220-225). Single nucleotide polymorphisms (SNPs) may also be used to identify the unique genetic composition of the XB33H12 and progeny varieties retaining or derived from that unique genetic composition. Various molecular marker techniques may be used in combination to enhance overall resolution.

Soybean DNA molecular marker linkage maps have been rapidly constructed and widely implemented in genetic studies. One such study is described in Cregan et al. (1999) Crop Science 39:1464-1490. Sequences and PCR conditions of SSR loci in soybean, as well as the most current genetic map, may be found in Soybase on the world wide web.

One use of molecular markers is quantitative trait loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection.

Production of Double Haploids

The production of double haploids can also be used for the development of plants with a homozygous phenotype in the breeding program. For example, a soybean plant for which variety XB33H12 or a soybean variety having all of the morphological and physiological characteristics of XB33H12 is a parent can be used to produce double haploid plants. Double haploids are produced by the doubling of a set of chromosomes (1N) from a heterozygous plant to produce a completely homozygous individual. For example, see Wan et al., "Efficient Production of Doubled Haploid Plants Through Colchicine Treatment of Anther-Derived Maize Callus" (1989) Theor Appl Genet 77:889-892, and US2003/0005479. This can be advantageous because the process omits the generations of selfing needed to obtain a homozygous plant from a heterozygous source.

Methods for obtaining haploid plants are disclosed in Kobayashi et al. (1980) J Heredity 71:9-14; Pollacsek (1992) Agronomie (Paris) 12:247-251; Cho-Un-Haing et al. (1996) J Plant Biol. 39:185-188; Verdoodt et al. (1998) Theor Appl Genet. 96:294-300; Genetic Manipulation in Plant Breeding, Proceedings International Symposium Organized by EUCARPIA, Sep. 8-13, 1985, Berlin, Germany; Chalyk et al. (1994) Maize Genet Coop. Newsletter 68:47. Double haploid technology in soybean is discussed in Croser et al. (2006) Crit. Rev Plant Sci 25:139-157; and Rodrigues et al. (2006) Brazilian Arc Biol Tech 49:537-545.

In some examples a process for making a substantially homozygous XB33H12 progeny plant by producing or obtaining a seed from the cross of XB33H12 and another soybean plant and applying double haploid methods to the F1 seed or F1 plant or to any successive filial generation is provided. Based on studies in maize, and currently being conducted in soybean, such methods would decrease the number of generations required to produce a variety with similar genetics or characteristics to XB33H12. See Bernardo and Kahler (2001) Theor. Appl. Genet. 102:986-992.

In particular, a process of making seed retaining the molecular marker profile of soybean variety XB33H12 is contemplated, such process comprising obtaining or producing F1 seed for which soybean variety XB33H12 is a parent, inducing doubled haploids to create progeny without the occurrence of meiotic segregation, obtaining the molecular marker profile of soybean variety XB33H12, and selecting progeny that retain the molecular marker profile of XB33H12.

Methods using seeds, plants, cells, or plant parts of variety XB33H12 in tissue culture are provided, as are the cultures, plants, parts, cells, and/or seeds derived therefrom. Tissue culture of various tissues of soybeans and regeneration of plants therefrom is well known and widely published. For example, see Komatsuda et al. (1991) Crop Sci. 31:333-337; Stephens et al. "Agronomic Evaluation of Tissue-Culture-Derived Soybean Plants" (1991) Theor. Appl. Genet. 82:633-635; Komatsuda et al. "Maturation and Germination of Somatic Embryos as Affected by Sucrose and Plant Growth Regulators in Soybeans *Glycine gracilis* Skvortz and *Glycine max* (L.) Merr." (1992) Plant Cell Tissue and Organ Culture 28:103-113; Dhir et al. "Regeneration of Fertile Plants from Protoplasts of Soybean (*Glycine max* L. Merr.): Genotypic Differences in Culture Response" (1992) Plant Cell Reports 11:285-289; Pandey et al. "Plant Regeneration from Leaf and Hypocotyl Explants of *Glycine wightii* (W. and A.) VERDC. var. *longicauda*" (1992) Japan J. Breed. 42:1-5; and Shetty et al. "Stimulation of In Vitro Shoot Organogenesis in *Glycine max* (Merrill.) by Allantoin and Amides" (1992) Plant Science 81:245-251; U.S. Pat. No. 5,024,944, to Collins et al.; and U.S. Pat. No. 5,008,200, to Ranch et al., the disclosures of which are hereby incorporated herein in their entirety by reference. Thus, another aspect is to provide cells which upon growth and differentiation produce soybean plants having the physiological and morphological characteristics of soybean variety XB33H12.

Soybean seeds, plants, and plant parts of variety XB33H12 may be cleaned and/or treated. The resulting seeds, plants, or plant parts produced by the cleaning and/or treating process(es) may exhibit enhanced yield characteristics. Enhanced yield characteristics can include one or more of the following: increased germination efficiency under normal and/or stress conditions, improved plant physiology, growth and/or development, such as water use efficiency, water retention efficiency, improved nitrogen use, enhanced carbon assimilation, improved photosynthesis, and accelerated maturation, and improved disease and/or pathogen tolerance. Yield characteristics can furthermore include enhanced plant architecture (under stress and non-stress conditions), including but not limited to early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield characteristics include seed composition, such as carbohydrate content, protein content, oil content and composition, nutritional value, reduction in anti-nutritional compounds, improved processibility, and better storage stability.

Cleaning a seed or seed cleaning refers to the removal of impurities and debris material from the harvested seed. Material to be removed from the seed includes but is not limited to soil, and plant waste, pebbles, weed seeds, broken soybean seeds, fungi, bacteria, insect material, including insect eggs, larvae, and parts thereof, and any other pests that exist with the harvested crop. The terms cleaning a seed or seed cleaning also refer to the removal of any debris or low quality, infested, or infected seeds and seeds of different species that are foreign to the sample.

Treating a seed or applying a treatment to a seed refers to the application of a composition to a seed as a coating or otherwise. The composition may be applied to the seed in a seed treatment at any time from harvesting of the seed to sowing of the seed. The composition may be applied using methods including but not limited to mixing in a container, mechanical application, tumbling, spraying, misting, and immersion. Thus, the composition may be applied as a powder, a crystalline, a ready-to-use, a slurry, a mist, and/or a soak. For a general discussion of techniques used to apply fungicides to seeds, see "Seed Treatment," 2d ed., (1986), edited by K. A Jeffs (chapter 9), herein incorporated by reference in its entirety. The composition to be used as a seed treatment can comprise one or more of a pesticide, a fungicide, an insecticide, a nematicide, an antimicrobial, an inoculant, a growth promoter, a polymer, a flow agent, a coating, or any combination thereof. General classes or family of seed treatment agents include triazoles, anilides, pyrazoles, carboxamides, succinate dehydrogenase inhibitors (SDHI), triazolinthiones, strobilurins, amides, and anthranilic diamides. In some examples, the seed treatment comprises trifloxystrobin, azoxystrobin, metalaxyl, metalaxyl-m, mefenoxam, fludioxinil, imidacloprid, thiamethoxam, thiabendazole, ipconazole, penflufen, sedaxane, prothioconazole, picoxystrobin, penthiopyrad, pyraclastrobin, xemium, *Rhizobia* spp., *Bradyrhizobium* spp. (e.g., *B. japonicum*), *Bacillus* spp. (e.g., *B. firmus, B. pumilus, B. subtilis*), lipochitooligosaccharide, clothianidin, cyazapyr, rynaxapyr, abamectin, and any combination thereof. In some examples the seed treatment comprises trifloxystrobin, metalaxyl, imidacloprid, *Bacillus* spp., and any combination thereof. In some examples the seed treatment comprises picoxystrobin, penthiopyrad, cyazapyr, ranaxapyr, and any combination thereof. In some examples, the seed treatment improves seed germination under normal and/or stress environments, early stand count, vigor, yield, root formation, nodulation, and any combination thereof. In some examples seed treatment reduces seed dust levels, insect damage, pathogen establishment and/or damage, plant virus infection and/or damage, and any combination thereof.

Soybean seeds, plants, and plant parts of variety XB33H12 may be used or processed for food, animal feed, or a raw material(s) for industry. Seeds from variety XB33H12 can be crushed, or a component of the seeds can be extracted in order to make a plant product, such as protein concentrate, protein isolate, soybean hulls, meal, flour, or oil for a food or feed product. Methods of producing a plant product, such as protein concentrate, protein isolate, soybean hulls, meal, flour, or oil for a food or feed product are provided. Also provided are the protein concentrate, protein isolate, soybean hulls, meal, flour, or oil produced by the methods.

Oil extracted from soybeans is used for cooking oil, margarine, and salad dressings. Soybean oil has a typical composition of 11% palmitic, 4% stearic, 25% oleic, 50% linoleic, and 9% linolenic fatty acid content. Industrial uses of soybean oil, which is typically subjected to further processing, include ingredients for paints, plastics, fibers, detergents, cosmetics, lubricants, and biodiesel fuel. Soybean oil may be split, inter-esterified, sulfurized, epoxidized, polymerized, ethoxylated, or cleaved. To produce oil, the harvested soybeans are cracked, adjusted for moisture content, rolled into flakes, and then the oil is solvent-extracted. The oil extract is refined, optionally blended and/or hydrogenated. Some soybean varieties have modified fatty acid profiles and can be used to produce soybean oil with a modified fatty acid composition. Oil with 3% or less linolenic acid is classified as low linolenic oil, oil with less than 1% linolenic acid is classified as ultra low linolenic oil. Oil with 70% or higher of oleic acid is classified as high oleic oil.

Soybeans are also used as a food source for both animals and humans. Soybeans are widely used as a source of protein for animal feed. The fibrous hull is removed from whole soybean and the oil is extracted. The remaining meal is a combination of carbohydrates and approximately 50% protein. This remaining meal is heat treated under well-established conditions and ground in a hammer mill. Soybean is a predominant source for livestock feed components.

In addition to soybean meal, soybean can be used to produce soy flour. Soy flour refers to defatted soybeans where special care was taken during desolventizing to minimize protein denaturation and to retain a high nitrogen solubility index (NSI) in making the flour. Soy flour is the typical starting material for production of soy concentrate and soy protein isolate. Defatted soy flour is obtained from solvent extracted flakes, and contains less than 1% oil. Full-fat soy flour is made from whole beans and contains about 18% to 20% oil. Low-fat soy flour is made by adding back some oil to defatted soy flour. The lipid content varies, but is usually between 4.5-9%. High-fat soy flour can also be produced by adding soybean oil to defatted flour at the level of 15%. Lecithinated soy flour is made by adding soybean lecithin to defatted, low-fat or high-fat soy flours to increase dispersibility and impart emulsifying properties.

For human consumption, soybean can be used to produce edible ingredients which serve as an alternative source of dietary protein. Common examples include milk, cheese, and meat substitutes. Additionally, soybean can be used to produce various types of fillers for meat and poultry products. Vitamins and/or minerals may be added to make soy products nutritionally more equivalent to animal protein sources as the protein quality is already roughly equivalent.

DEPOSITS

Applicant made a deposit of seeds of Soybean Variety XB33H12 with the American Type Culture Collection (ATCC), Manassas, Va. 20110 USA, ATCC Deposit No. PTA-120188. The seeds to be deposited with the ATCC on Apr. 16, 2013 were taken from the seed stock maintained by Pioneer Hi-Bred International, Inc., 7250 NW 62nd Avenue, Johnston, Iowa 50131 since prior to the filing date of this application. Access to this seed stock will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. §1.808. This deposit of Soybean Variety XB33H12 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all the requirements of 37 C.F.R. §§1.801-1.809, including providing an indication of the viability of the sample upon deposit. Applicant has no authority to waive any restrictions imposed by law on the transfer of biological material or its transportation in commerce. Applicant does not waive any infringement of their rights granted under this patent or under the Plant Variety Protection Act (7 USC 2321 et seq.).

All publications, patents, and patent applications mentioned in the specification are indicative of the level of those skilled in the art to which this invention pertains. All such publications, patents, and patent applications are incorporated by reference herein for the purpose cited to the same extent as if each was specifically and individually indicated to be incorporated by reference herein.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications, and alterations may be applied to the compositions and/or methods described herein without departing from the true spirit, concept, and scope of the invention.

As used herein, the terms "comprises," "comprising," "includes," "including," "has," "having," "contains", "containing," "characterized by" or any other variation thereof, are intended to cover a non-exclusive inclusion. For example, a composition, mixture, process, method, article, or apparatus that comprises a list of elements is not necessarily limited to only those elements but may include other elements not expressly listed or inherent to such composition, mixture, process, method, article, or apparatus. The transitional phrase "consisting of" excludes any element, step, or ingredient other than those recited except for impurities ordinarily associated therewith. When the phrase "consisting of" appears in a clause of the body of a claim, rather than immediately following the preamble, it limits only the element set forth in that clause; other elements are not excluded from the claim as a whole. The transitional phrase "consisting essentially of" is used to define a composition, method or apparatus that includes materials, steps, features, components, or elements, in addition to those literally disclosed, provided that these additional materials, steps, features, components, or elements do not materially affect the basic characteristic(s).

Unless expressly stated to the contrary, "or" is used as an inclusive term. For example, a condition A or B is satisfied by any one of the following: A is true (or present) and B is false (or not present), A is false (or not present) and B is true (or present), and both A and B are true (or present). The indefinite articles "a" and "an" preceding an element or component are nonrestrictive regarding the number of instances (i.e., occurrences) of the element or component. Therefore "a" or "an" should be read to include one or at least one, and the singular word form of the element or component also includes the plural unless the number is obviously meant to be singular.

TABLE 1

| Variety Description Information | |
| --- | --- |
| Current Variety Name | XB33H12 |
| Relative Maturity | 3.3 |
| Canadian Heat Units | 3350 |
| Herbicide Resistance | Gly |
| Harvest Standability | 7 |
| Emergence Score | 66 |
| Hypocotyl Score | 66 |
| *Phytophthora* Gene | 1K |
| *Phytophthora* Field | 6 |
| Brown Stem Rot | |
| Iron Chlorosis | 4 |
| Downy Mildew | |
| White Mold | |
| Sudden Death Syndrome | 6 |
| Cyst Nematode Race1 | |
| Cyst Nematode Race2 | |
| Cyst Nematode Race3 | 99 |
| Cyst Nematode Race5 | |

TABLE 1-continued

| Variety Description Information | |
| --- | --- |
| Current Variety Name | XB33H12 |
| Cyst Nematode Race14 | 99 |
| Aphid Antibosis | 5 |
| Charcoal Rot Drought | 55 |
| Root-knot Southern | |
| Root-knot Peanut | |
| Stem Canker Genetic | |
| Frogeye Leaf Spot | 66 |
| Frogeye Leaf Spot Lab | |
| *Cercospora* Field | |
| Chloride Sensitivity | |
| Canopy Width | 6 |
| Shattering | |
| Height/Maturity | 5 |
| Plant Growth Habit | Ind |
| Oil/Meal Type | |
| % Protein @ 13% H2O | 33.5 |
| % Oil @ 13% H2O | 19.1 |
| Seed Size Score | 8 |
| Seed Size Range | |
| Flower Color | W |
| Pubescence Color | L |
| Hila Color | BL |
| Pod Color | BR |
| Seed Coat Luster | D |

TABLE 2

| VARIETY COMPARISON DATA | | | | | | |
| --- | --- | --- | --- | --- | --- | --- |
| Variety1 | Variety2 | Statistic | YIELD | MATABS | HGT | LDGSEV |
| XB33H12 | 93M42 | Mean1 | 56.6 | 134.4 | 36.4 | 7.1 |
| XB33H12 | 93M42 | Mean2 | 53.8 | 136.3 | 39.3 | 7.8 |
| XB33H12 | 93M42 | # Locs | 36 | 10 | 7 | 8 |
| XB33H12 | 93M42 | # Reps | 72 | 17 | 12 | 14 |
| XB33H12 | 93M42 | # Years | 1 | 1 | 1 | 1 |
| XB33H12 | 93M42 | SE Diff | 0.77 | 1.16 | 0.93 | 0.23 |
| XB33H12 | 93M42 | Prob | 0.0012 | 0.1356 | 0.0219 | 0.0203 |
| XB33H12 | 93M43 | Mean1 | 56.7 | 134.4 | 36.4 | 7.1 |
| XB33H12 | 93M43 | Mean2 | 52.5 | 135.3 | 37.7 | 6 |
| XB33H12 | 93M43 | # Locs | 34 | 10 | 7 | 8 |
| XB33H12 | 93M43 | # Reps | 70 | 17 | 13 | 15 |
| XB33H12 | 93M43 | # Years | 1 | 1 | 1 | 1 |
| XB33H12 | 93M43 | SE Diff | 0.81 | 0.99 | 1.21 | 0.38 |
| XB33H12 | 93M43 | Prob | 0 | 0.3624 | 0.3304 | 0.0199 |
| XB33H12 | 93M61 | Mean1 | 53.1 | | | |
| XB33H12 | 93M61 | Mean2 | 54 | | | |
| XB33H12 | 93M61 | # Locs | 4 | | | |
| XB33H12 | 93M61 | # Reps | 8 | | | |
| XB33H12 | 93M61 | # Years | 1 | | | |
| XB33H12 | 93M61 | SE Diff | 1.87 | | | |
| XB33H12 | 93M61 | Prob | 0.6774 | | | |
| XB33H12 | 93Y20 | Mean1 | 56.6 | 134.4 | 36.4 | 7.1 |
| XB33H12 | 93Y20 | Mean2 | 54.9 | 134 | 38.6 | 5.8 |
| XB33H12 | 93Y20 | # Locs | 36 | 10 | 7 | 8 |
| XB33H12 | 93Y20 | # Reps | 73 | 17 | 13 | 15 |
| XB33H12 | 93Y20 | # Years | 1 | 1 | 1 | 1 |
| XB33H12 | 93Y20 | SE Diff | 0.71 | 0.81 | 0.53 | 0.35 |
| XB33H12 | 93Y20 | Prob | 0.0228 | 0.6342 | 0.006 | 0.0057 |
| XB33H12 | 93Y22 | Mean1 | 56.6 | 134.4 | 36.4 | 7.1 |
| XB33H12 | 93Y22 | Mean2 | 56.4 | 134.8 | 36.6 | 7 |
| XB33H12 | 93Y22 | # Locs | 36 | 10 | 7 | 8 |
| XB33H12 | 93Y22 | # Reps | 73 | 17 | 13 | 15 |
| XB33H12 | 93Y22 | # Years | 1 | 1 | 1 | 1 |
| XB33H12 | 93Y22 | SE Diff | 0.77 | 0.93 | 0.82 | 0.23 |
| XB33H12 | 93Y22 | Prob | 0.7966 | 0.6408 | 0.8015 | 0.5983 |
| XB33H12 | 93Y40 | Mean1 | 56.2 | 134.4 | 36.4 | 7.1 |
| XB33H12 | 93Y40 | Mean2 | 53.4 | 135.2 | 36.1 | 7.5 |
| XB33H12 | 93Y40 | # Locs | 40 | 10 | 7 | 8 |
| XB33H12 | 93Y40 | # Reps | 83 | 17 | 13 | 15 |
| XB33H12 | 93Y40 | # Years | 1 | 1 | 1 | 1 |
| XB33H12 | 93Y40 | SE Diff | 0.69 | 0.91 | 0.89 | 0.38 |
| XB33H12 | 93Y40 | Prob | 0.0002 | 0.4009 | 0.7794 | 0.3506 |

TABLE 2-continued

VARIETY COMPARISON DATA

| Variety1 | Variety2 | Statistic | YIELD | MATABS | HGT | LDGSEV |
|---|---|---|---|---|---|---|
| XB33H12 | 93Y52 | Mean1 | 56.6 | 134.4 | 36.4 | 7.1 |
| XB33H12 | 93Y52 | Mean2 | 54.5 | 138.4 | 35.2 | 6.8 |
| XB33H12 | 93Y52 | # Locs | 36 | 10 | 7 | 8 |
| XB33H12 | 93Y52 | # Reps | 72 | 17 | 13 | 15 |
| XB33H12 | 93Y52 | # Years | 1 | 1 | 1 | 1 |
| XB33H12 | 93Y52 | SE Diff | 1.04 | 0.79 | 0.65 | 0.38 |
| XB33H12 | 93Y52 | Prob | 0.0522 | 0.0006 | 0.1065 | 0.4348 |
| XB33H12 | 93Y60 | Mean1 | 56.2 | 134.4 | 36.4 | 7.1 |
| XB33H12 | 93Y60 | Mean2 | 55.8 | 138.2 | 38.3 | 7.9 |
| XB33H12 | 93Y60 | # Locs | 40 | 10 | 7 | 8 |
| XB33H12 | 93Y60 | # Reps | 83 | 17 | 13 | 15 |
| XB33H12 | 93Y60 | # Years | 1 | 1 | 1 | 1 |
| XB33H12 | 93Y60 | SE Diff | 0.71 | 0.94 | 0.93 | 0.16 |
| XB33H12 | 93Y60 | Prob | 0.5193 | 0.003 | 0.0831 | 0.0025 |
| XB33H12 | RJS33001 | Mean1 | 56.6 | 134.4 | 36.4 | 7.1 |
| XB33H12 | RJS33001 | Mean2 | 51.5 | 134.6 | 37.3 | 5.4 |
| XB33H12 | RJS33001 | # Locs | 36 | 10 | 7 | 8 |
| XB33H12 | RJS33001 | # Reps | 73 | 17 | 13 | 15 |
| XB33H12 | RJS33001 | # Years | 1 | 1 | 1 | 1 |
| XB33H12 | RJS33001 | SE Diff | 1.1 | 0.72 | 1.31 | 0.6 |
| XB33H12 | RJS33001 | Prob | 0 | 0.7884 | 0.525 | 0.0269 |
| XB33H12 | RJS33002 | Mean1 | 56.6 | 134.4 | 36.4 | 7.1 |
| XB33H12 | RJS33002 | Mean2 | 55.7 | 134.5 | 38.6 | 6.3 |
| XB33H12 | RJS33002 | # Locs | 36 | 10 | 7 | 8 |
| XB33H12 | RJS33002 | # Reps | 74 | 17 | 13 | 15 |
| XB33H12 | RJS33002 | # Years | 1 | 1 | 1 | 1 |
| XB33H12 | RJS33002 | SE Diff | 0.68 | 0.56 | 0.75 | 0.41 |
| XB33H12 | RJS33002 | Prob | 0.2 | 0.8614 | 0.0251 | 0.0887 |
| XB33H12 | RJS34001 | Mean1 | 56.2 | 134.4 | 36.4 | 7.1 |
| XB33H12 | RJS34001 | Mean2 | 55.5 | 135 | 38.2 | 6.6 |
| XB33H12 | RJS34001 | # Locs | 40 | 10 | 7 | 8 |
| XB33H12 | RJS34001 | # Reps | 81 | 17 | 13 | 15 |
| XB33H12 | RJS34001 | # Years | 1 | 1 | 1 | 1 |
| XB33H12 | RJS34001 | SE Diff | 0.59 | 0.64 | 0.74 | 0.33 |
| XB33H12 | RJS34001 | Prob | 0.2406 | 0.3732 | 0.0486 | 0.1705 |
| XB33H12 | RJS34006 | Mean1 | 56.2 | 134.4 | 36.4 | 7.1 |
| XB33H12 | RJS34006 | Mean2 | 54.6 | 136.9 | 37.9 | 6.7 |
| XB33H12 | RJS34006 | # Locs | 40 | 10 | 7 | 8 |
| XB33H12 | RJS34006 | # Reps | 82 | 17 | 13 | 15 |
| XB33H12 | RJS34006 | # Years | 1 | 1 | 1 | 1 |
| XB33H12 | RJS34006 | SE Diff | 0.63 | 0.83 | 0.76 | 0.58 |
| XB33H12 | RJS34006 | Prob | 0.0122 | 0.0144 | 0.0914 | 0.4739 |
| XB33H12 | RJS35001 | Mean1 | 53.1 | | | |
| XB33H12 | RJS35001 | Mean2 | 54.5 | | | |
| XB33H12 | RJS35001 | # Locs | 4 | | | |
| XB33H12 | RJS35001 | # Reps | 8 | | | |
| XB33H12 | RJS35001 | # Years | 1 | | | |
| XB33H12 | RJS35001 | SE Diff | 1.98 | | | |
| XB33H12 | RJS35001 | Prob | 0.5483 | | | |

TABLE 2

VARIETY COMPARISON DATA

| Variety1 | Variety2 | Statistic | SPLB | PROTN % | OIL % | FEY |
|---|---|---|---|---|---|---|
| XB33H12 | 93M42 | Mean1 | 3432 | 33.37 | 19.16 | 5.5 |
| XB33H12 | 93M42 | Mean2 | 3288 | 34.99 | 17.87 | 8.5 |
| XB33H12 | 93M42 | # Locs | 4 | 5 | 5 | 1 |
| XB33H12 | 93M42 | # Reps | 4 | 5 | 5 | 2 |
| XB33H12 | 93M42 | # Years | 1 | 1 | 1 | 1 |
| XB33H12 | 93M42 | SE Diff | 181.4 | 0.884 | 0.385 | |
| XB33H12 | 93M42 | Prob | 0.4846 | 0.1412 | 0.0284 | |
| XB33H12 | 93M43 | Mean1 | 3432 | 33.37 | 19.16 | 5.5 |
| XB33H12 | 93M43 | Mean2 | 3127 | 33.14 | 18.77 | 8.5 |
| XB33H12 | 93M43 | # Locs | 4 | 5 | 5 | 1 |
| XB33H12 | 93M43 | # Reps | 4 | 5 | 5 | 2 |
| XB33H12 | 93M43 | # Years | 1 | 1 | 1 | 1 |
| XB33H12 | 93M43 | SE Diff | 168.1 | 0.516 | 0.159 | |
| XB33H12 | 93M43 | Prob | 0.1675 | 0.6752 | 0.0706 | |
| XB33H12 | 93M61 | Mean1 | | | | |
| XB33H12 | 93M61 | Mean2 | | | | |
| XB33H12 | 93M61 | # Locs | | | | |

TABLE 2-continued

VARIETY COMPARISON DATA

| Variety1 | Variety2 | Statistic | SPLB | PROTN % | OIL % | FEY |
|---|---|---|---|---|---|---|
| XB33H12 | 93M61 | # Reps | | | | |
| XB33H12 | 93M61 | # Years | | | | |
| XB33H12 | 93M61 | SE Diff | | | | |
| XB33H12 | 93M61 | Prob | | | | |
| XB33H12 | 93Y20 | Mean1 | 3432 | 33.37 | 19.16 | 5.5 |
| XB33H12 | 93Y20 | Mean2 | 3027 | 33.23 | 19.23 | 8.5 |
| XB33H12 | 93Y20 | # Locs | 4 | 5 | 5 | 1 |
| XB33H12 | 93Y20 | # Reps | 4 | 5 | 5 | 2 |
| XB33H12 | 93Y20 | # Years | 1 | 1 | 1 | 1 |
| XB33H12 | 93Y20 | SE Diff | 216.6 | 0.674 | 0.216 | |
| XB33H12 | 93Y20 | Prob | 0.158 | 0.8507 | 0.7542 | |
| XB33H12 | 93Y22 | Mean1 | 3430 | 34.18 | 18.55 | 5.5 |
| XB33H12 | 93Y22 | Mean2 | 3294 | 35.4 | 18.47 | 7 |
| XB33H12 | 93Y22 | # Locs | 3 | 4 | 4 | 1 |
| XB33H12 | 93Y22 | # Reps | 3 | 4 | 4 | 2 |
| XB33H12 | 93Y22 | # Years | 1 | 1 | 1 | 1 |
| XB33H12 | 93Y22 | SE Diff | 203.6 | 0.414 | 0.235 | |
| XB33H12 | 93Y22 | Prob | 0.5751 | 0.0613 | 0.7561 | |
| XB33H12 | 93Y40 | Mean1 | 3432 | 32.81 | 19.91 | 5.5 |
| XB33H12 | 93Y40 | Mean2 | 3011 | 33.33 | 19.33 | 5.5 |
| XB33H12 | 93Y40 | # Locs | 4 | 3 | 3 | 1 |
| XB33H12 | 93Y40 | # Reps | 4 | 3 | 3 | 2 |
| XB33H12 | 93Y40 | # Years | 1 | 1 | 1 | 1 |
| XB33H12 | 93Y40 | SE Diff | 158 | 1.363 | 0.531 | |
| XB33H12 | 93Y40 | Prob | 0.0762 | 0.7424 | 0.3898 | |
| XB33H12 | 93Y52 | Mean1 | 3432 | 33.37 | 19.16 | 5.5 |
| XB33H12 | 93Y52 | Mean2 | 3308 | 33.74 | 19.16 | 9 |
| XB33H12 | 93Y52 | # Locs | 4 | 5 | 5 | 1 |
| XB33H12 | 93Y52 | # Reps | 4 | 5 | 5 | 2 |
| XB33H12 | 93Y52 | # Years | 1 | 1 | 1 | 1 |
| XB33H12 | 93Y52 | SE Diff | 76.5 | 0.51 | 0.201 | |
| XB33H12 | 93Y52 | Prob | 0.2042 | 0.5035 | 0.9795 | |
| XB33H12 | 93Y60 | Mean1 | 3432 | 33.31 | 19.42 | 5.5 |
| XB33H12 | 93Y60 | Mean2 | 2889 | 33.2 | 19.32 | 8 |
| XB33H12 | 93Y60 | # Locs | 4 | 4 | 4 | 1 |
| XB33H12 | 93Y60 | # Reps | 4 | 4 | 4 | 2 |
| XB33H12 | 93Y60 | # Years | 1 | 1 | 1 | 1 |
| XB33H12 | 93Y60 | SE Diff | 168.8 | 0.62 | 0.319 | |
| XB33H12 | 93Y60 | Prob | 0.0488 | 0.8732 | 0.792 | |
| XB33H12 | RJS33001 | Mean1 | 3432 | 32.81 | 19.91 | 5.5 |
| XB33H12 | RJS33001 | Mean2 | 2971 | 32.41 | 20.23 | 9 |
| XB33H12 | RJS33001 | # Locs | 4 | 3 | 3 | 1 |
| XB33H12 | RJS33001 | # Reps | 4 | 3 | 3 | 2 |
| XB33H12 | RJS33001 | # Years | 1 | 1 | 1 | 1 |
| XB33H12 | RJS33001 | SE Diff | 190.6 | 1.303 | 0.484 | |
| XB33H12 | RJS33001 | Prob | 0.0944 | 0.7861 | 0.5773 | |
| XB33H12 | RJS33002 | Mean1 | 3432 | 33.37 | 19.16 | 5.5 |
| XB33H12 | RJS33002 | Mean2 | 3097 | 32.5 | 19.15 | 3 |
| XB33H12 | RJS33002 | # Locs | 4 | 5 | 5 | 1 |
| XB33H12 | RJS33002 | # Reps | 4 | 5 | 5 | 2 |
| XB33H12 | RJS33002 | # Years | 1 | 1 | 1 | 1 |
| XB33H12 | RJS33002 | SE Diff | 144.2 | 0.428 | 0.291 | |
| XB33H12 | RJS33002 | Prob | 0.1029 | 0.1122 | 0.9904 | |
| XB33H12 | RJS34001 | Mean1 | 3432 | 33.31 | 19.42 | 5.5 |
| XB33H12 | RJS34001 | Mean2 | 3303 | 33 | 19.35 | 3 |
| XB33H12 | RJS34001 | # Locs | 4 | 4 | 4 | 1 |
| XB33H12 | RJS34001 | # Reps | 4 | 4 | 4 | 2 |
| XB33H12 | RJS34001 | # Years | 1 | 1 | 1 | 1 |
| XB33H12 | RJS34001 | SE Diff | 176.3 | 0.388 | 0.27 | |
| XB33H12 | RJS34001 | Prob | 0.5179 | 0.4826 | 0.8166 | |
| XB33H12 | RJS34006 | Mean1 | 3317 | 33.47 | 19.27 | 5.5 |
| XB33H12 | RJS34006 | Mean2 | 2889 | 33.81 | 19 | 5 |
| XB33H12 | RJS34006 | # Locs | 5 | 5 | 5 | 1 |
| XB33H12 | RJS34006 | # Reps | 5 | 5 | 5 | 2 |
| XB33H12 | RJS34006 | # Years | 1 | 1 | 1 | 1 |
| XB33H12 | RJS34006 | SE Diff | 129.5 | 0.51 | 0.259 | |
| XB33H12 | RJS34006 | Prob | 0.03 | 0.5478 | 0.3517 | |
| XB33H12 | RJS35001 | Mean1 | | | | |
| XB33H12 | RJS35001 | Mean2 | | | | |
| XB33H12 | RJS35001 | # Locs | | | | |
| XB33H12 | RJS35001 | # Reps | | | | |
| XB33H12 | RJS35001 | # Years | | | | |
| XB33H12 | RJS35001 | SE Diff | | | | |
| XB33H12 | RJS35001 | Prob | | | | |

TABLE 2

VARIETY COMPARISON DATA

| Variety1 | Variety2 | Statistic | CRDC |
|---|---|---|---|
| XB33H12 | 93M42 | Mean1 | 7 |
| XB33H12 | 93M42 | Mean2 | 8 |
| XB33H12 | 93M42 | #Locs | 1 |
| XB33H12 | 93M42 | #Reps | 1 |
| XB33H12 | 93M42 | #Years | 1 |
| XB33H12 | 93M42 | SE Diff | |
| XB33H12 | 93M42 | Prob | |
| XB33H12 | 93M43 | Mean1 | 7 |
| XB33H12 | 93M43 | Mean2 | 7 |
| XB33H12 | 93M43 | #Locs | 1 |
| XB33H12 | 93M43 | #Reps | 1 |
| XB33H12 | 93M43 | #Years | 1 |
| XB33H12 | 93M43 | SE Diff | |
| XB33H12 | 93M43 | Prob | |
| XB33H12 | 93M61 | Mean1 | |
| XB33H12 | 93M61 | Mean2 | |
| XB33H12 | 93M61 | #Locs | |
| XB33H12 | 93M61 | #Reps | |
| XB33H12 | 93M61 | #Years | |
| XB33H12 | 93M61 | SE Diff | |
| XB33H12 | 93M61 | Prob | |
| XB33H12 | 93Y20 | Mean1 | 7 |
| XB33H12 | 93Y20 | Mean2 | 7 |
| XB33H12 | 93Y20 | #Locs | 1 |
| XB33H12 | 93Y20 | #Reps | 1 |
| XB33H12 | 93Y20 | #Years | 1 |
| XB33H12 | 93Y20 | SE Diff | |
| XB33H12 | 93Y20 | Prob | |
| XB33H12 | 93Y22 | Mean1 | 7 |
| XB33H12 | 93Y22 | Mean2 | 6 |
| XB33H12 | 93Y22 | #Locs | 1 |
| XB33H12 | 93Y22 | #Reps | 1 |
| XB33H12 | 93Y22 | #Years | 1 |
| XB33H12 | 93Y22 | SE Diff | |
| XB33H12 | 93Y22 | Prob | |
| XB33H12 | 93Y40 | Mean1 | 7 |
| XB33H12 | 93Y40 | Mean2 | 5 |
| XB33H12 | 93Y40 | #Locs | 1 |
| XB33H12 | 93Y40 | #Reps | 1 |
| XB33H12 | 93Y40 | #Years | 1 |
| XB33H12 | 93Y40 | SE Diff | |
| XB33H12 | 93Y40 | Prob | |
| XB33H12 | 93Y52 | Mean1 | 7 |
| XB33H12 | 93Y52 | Mean2 | 6 |
| XB33H12 | 93Y52 | #Locs | 1 |
| XB33H12 | 93Y52 | #Reps | 1 |
| XB33H12 | 93Y52 | #Years | 1 |
| XB33H12 | 93Y52 | SE Diff | |
| XB33H12 | 93Y52 | Prob | |
| XB33H12 | 93Y60 | Mean1 | 7 |
| XB33H12 | 93Y60 | Mean2 | 7 |
| XB33H12 | 93Y60 | #Locs | 1 |
| XB33H12 | 93Y60 | #Reps | 1 |
| XB33H12 | 93Y60 | #Years | 1 |
| XB33H12 | 93Y60 | SE Diff | |
| XB33H12 | 93Y60 | Prob | |
| XB33H12 | RJS33001 | Mean1 | 7 |
| XB33H12 | RJS33001 | Mean2 | 8 |
| XB33H12 | RJS33001 | #Locs | 1 |
| XB33H12 | RJS33001 | #Reps | 1 |
| XB33H12 | RJS33001 | #Years | 1 |
| XB33H12 | RJS33001 | SE Diff | |
| XB33H12 | RJS33001 | Prob | |
| XB33H12 | RJS33002 | Mean1 | 7 |
| XB33H12 | RJS33002 | Mean2 | 5 |
| XB33H12 | RJS33002 | #Locs | 1 |
| XB33H12 | RJS33002 | #Reps | 1 |
| XB33H12 | RJS33002 | #Years | 1 |
| XB33H12 | RJS33002 | SE Diff | |
| XB33H12 | RJS33002 | Prob | |
| XB33H12 | RJS34001 | Mean1 | 7 |
| XB33H12 | RJS34001 | Mean2 | 7 |
| XB33H12 | RJS34001 | #Locs | 1 |
| XB33H12 | RJS34001 | #Reps | 1 |
| XB33H12 | RJS34001 | #Years | 1 |
| XB33H12 | RJS34001 | SE Diff | |
| XB33H12 | RJS34001 | Prob | |
| XB33H12 | RJS34006 | Mean1 | 7 |
| XB33H12 | RJS34006 | Mean2 | 3 |
| XB33H12 | RJS34006 | #Locs | 1 |
| XB33H12 | RJS34006 | #Reps | 1 |
| XB33H12 | RJS34006 | #Years | 1 |
| XB33H12 | RJS34006 | SE Diff | |
| XB33H12 | RJS34006 | Prob | |
| XB33H12 | RJS35001 | Mean1 | |
| XB33H12 | RJS35001 | Mean2 | |
| XB33H12 | RJS35001 | #Locs | |
| XB33H12 | RJS35001 | #Reps | |
| XB33H12 | RJS35001 | #Years | |
| XB33H12 | RJS35001 | SE Diff | |
| XB33H12 | RJS35001 | Prob | |

TABLE 3

Soybean SSR Marker Set

| | | | |
|---|---|---|---|
| SAC1006 | SATT129 | SATT243 | SATT334 |
| SAC1611 | SATT130 | SATT247 | SATT335 |
| SAC1634 | SATT131 | SATT249 | SATT336 |
| SAC1677 | SATT133 | SATT250 | SATT338 |
| SAC1699 | SATT142 | SATT251 | SATT339 |
| SAC1701 | SATT144 | SATT255 | SATT343 |
| SAC1724 | SATT146 | SATT256 | SATT346 |
| SAT_084 | SATT147 | SATT257 | SATT347 |
| SAT_090 | SATT150 | SATT258 | SATT348 |
| SAT_104 | SATT151 | SATT259 | SATT352 |
| SAT_117 | SATT153 | SATT262 | SATT353 |
| SAT_142-DB | SATT155 | SATT263 | SATT355 |
| SAT_189 | SATT156 | SATT264 | SATT356 |
| SAT_222-DB | SATT165 | SATT265 | SATT357 |
| SAT_261 | SATT166 | SATT266 | SATT358 |
| SAT_270 | SATT168 | SATT267 | SATT359 |
| SAT_271-DB | SATT172 | SATT270 | SATT361 |
| SAT_273-DB | SATT175 | SATT272 | SATT364 |
| SAT_275-DB | SATT181 | SATT274 | SATT367 |
| SAT_299 | SATT183 | SATT279 | SATT369 |
| SAT_301 | SATT186 | SATT280 | SATT373 |
| SAT_311-DB | SATT190 | SATT282 | SATT378 |
| SAT_317 | SATT191 | SATT284 | SATT380 |
| SAT_319-DB | SATT193 | SATT285 | SATT383 |
| SAT_330-DB | SATT195 | SATT287 | SATT385 |
| SAT_331-DB | SATT196 | SATT292 | SATT387 |
| SAT_343 | SATT197 | SATT295 | SATT389 |
| SAT_351 | SATT199 | SATT299 | SATT390 |
| SAT_366 | SATT202 | SATT300 | SATT391 |
| SAT_381 | SATT203 | SATT307 | SATT393 |
| SATT040 | SATT204 | SATT314 | SATT398 |
| SATT042 | SATT212 | SATT319 | SATT399 |
| SATT050 | SATT213 | SATT321 | SATT406 |
| SATT092 | SATT216 | SATT322 | SATT409 |
| SATT102 | SATT219 | SATT326 | SATT411 |
| SATT108 | SATT221 | SATT327 | SATT412 |
| SATT109 | SATT225 | SATT328 | SATT413 |
| SATT111 | SATT227 | SATT330 | SATT414 |
| SATT115 | SATT228 | SATT331 | SATT415 |
| SATT122 | SATT230 | SATT332 | SATT417 |
| SATT127 | SATT233 | SATT333 | SATT418 |
| SATT420 | SATT508 | SATT583 | SATT701 |
| SATT421 | SATT509 | SATT584 | SATT708-TB |
| SATT422 | SATT510 | SATT586 | SATT712 |
| SATT423 | SATT511 | SATT587 | SATT234 |
| SATT429 | SATT512 | SATT590 | SATT240 |
| SATT431 | SATT513 | SATT591 | SATT242 |
| SATT432 | SATT514 | SATT594 | |
| SATT433 | SATT515 | SATT595 | |
| SATT436 | SATT517 | SATT596 | |
| SATT440 | SATT519 | SATT597 | |
| SATT441 | SATT522 | SATT598 | |
| SATT442 | SATT523 | SATT601 | |

TABLE 3-continued

Soybean SSR Marker Set

| | | |
|---|---|---|
| SATT444 | SATT524 | SATT602 |
| SATT448 | SATT526 | SATT608 |
| SATT451 | SATT529 | SATT613 |
| SATT452 | SATT533 | SATT614 |
| SATT454 | SATT534 | SATT617 |
| SATT455 | SATT536 | SATT618 |
| SATT457 | SATT537 | SATT628 |
| SATT460 | SATT540 | SATT629 |
| SATT461 | SATT544 | SATT630 |
| SATT464 | SATT545 | SATT631 |
| SATT466 | SATT546 | SATT632-TB |
| SATT467 | SATT548 | SATT633 |
| SATT469 | SATT549 | SATT634 |
| SATT470 | SATT550 | SATT636 |
| SATT471 | SATT551 | SATT640-TB |
| SATT473 | SATT552 | SATT651 |
| SATT475 | SATT555 | SATT654 |
| SATT476 | SATT556 | SATT655-TB |
| SATT477 | SATT557 | SATT656 |
| SATT478 | SATT558 | SATT660 |
| SATT479 | SATT565 | SATT661-TB |
| SATT480 | SATT566 | SATT662 |
| SATT487 | SATT567 | SATT665 |
| SATT488 | SATT568 | SATT666 |
| SATT491 | SATT569 | SATT667 |
| SATT492 | SATT570 | SATT672 |
| SATT493 | SATT572 | SATT675 |
| SATT495 | SATT573 | SATT677 |
| SATT497 | SATT576 | SATT678 |
| SATT503 | SATT578 | SATT680 |
| SATT506 | SATT581 | SATT684 |
| SATT507 | SATT582 | SATT685 |

TABLE 4

BREEDING HISTORY FOR XB33H12

Bi-parental cross
F1 growout harvested in bulk
F2 modified single seed descent
F3 single plant selections made
Progeny row yield test
Regional yield testing
Regional yield testing
Purification - individual plant rows harvested and advanced
Purification - bulk harvested
Advanced yield testing
Bulk breeder's seed increase
Foundation seed production
Elite yield testing

What is claimed:

1. A plant, a plant part, or a seed of soybean variety XB33H12, representative seed of said soybean variety XB33H12 having been deposited under ATCC Accession Number PTA-120188.

2. A soybean seed obtained by introducing a transgene into soybean variety XB33H12, representative seed of said soybean variety XB33H12 having been deposited under ATCC Accession Number PTA-120188.

3. The seed of claim 2, wherein the transgene confers a trait selected from the group consisting of male sterility, site-specific recombination, abiotic stress tolerance, altered phosphorus, altered antioxidants, altered fatty acids, altered essential amino acids, altered carbohydrates, herbicide resistance, insect resistance, and disease resistance.

4. A soybean plant, or a part thereof, produced by growing the seed of claim 1.

5. A soybean plant, or a part thereof, produced by growing the seed of claim 2.

6. A method for developing a second soybean plant comprising applying plant breeding techniques to a first soybean plant, or parts thereof, wherein said first soybean plant is the soybean plant of claim 1, and wherein application of said techniques results in development of said second soybean plant.

7. A method for producing soybean seed comprising crossing two soybean plants and harvesting the resultant soybean seed, wherein at least one soybean plant is the soybean plant of claim 1.

8. The soybean seed produced by the method of claim 7.

9. A soybean plant, or a part thereof, produced by growing said seed of claim 8.

10. A method for developing a second soybean plant in a soybean plant breeding program comprising applying plant breeding techniques to a first soybean plant, or parts thereof, wherein said first soybean plant is the soybean plant of claim 9, and wherein application of said techniques results in development of said second soybean plant.

11. A method of producing a soybean plant comprising a locus conversion, the method comprising introducing a locus conversion into the plant of claim 1, wherein said locus conversion provides a trait selected from the group consisting of male sterility, site-specific recombination, abiotic stress tolerance, altered phosphorus, altered antioxidants, altered fatty acids, altered essential amino acids, altered carbohydrates, herbicide resistance, insect resistance, and disease resistance.

12. A herbicide resistant soybean plant produced by the method of claim 11, wherein said so bean plant comprises all of the physiological and morphological characteristics of soybean variety XB33H12 when grown in the same environmental characteristics.

13. A disease resistant soybean plant produced by the method of claim 11, wherein said so bean plant comprises all of the physiological and morphological characteristics of soybean variety XB33H12 when grown in the same environmental characteristics.

14. An insect resistant soybean plant produced by the method of claim 11, wherein said soybean plant comprises all of the physiological and morphological characteristics of soybean variety XB33H12 when grown in the same environmental characteristics.

15. The soybean plant of claim 14, wherein the locus conversion comprises a transgene encoding a *Bacillus thuringiensis* (Bt) endotoxin.

16. A soybean plant, or a part thereof, expressing all the physiological and morphological characteristics of soybean variety XB33H12, representative seed of said soybean variety XB33H12 having been deposited under ATCC Accession Number PTA-120188.

17. A method comprising isolating nucleic acids from a plant, a plant part, or a seed of soybean variety XB33H12, representative seed of said soybean variety XB33H12 having been deposited under ATCC Accession Number PTA-120188, analyzing said nucleic acids to produce data, and recording the data for XB33H12.

18. The method of claim 17, wherein the data is recorded on a computer readable medium.

19. The method of claim 17, wherein the data is a nucleic acid sequence, a marker profile, a haplotype, or any combination thereof.

* * * * *